United States Patent [19]

Tibbetts et al.

[11] Patent Number: 5,365,455
[45] Date of Patent: Nov. 15, 1994

[54] METHOD AND APPARATUS FOR AUTOMATIC NUCLEIC ACID SEQUENCE DETERMINATION

[75] Inventors: Clark Tibbetts, Nashville; John M. Bowling, Murfreesboro, both of Tenn.

[73] Assignee: Vanderbilt University, Nashville, Tenn.

[21] Appl. No.: 763,457

[22] Filed: Sep. 20, 1991

[51] Int. Cl.$^5$ .............................................. G06G 7/58
[52] U.S. Cl. .............................. 364/497; 364/413.01; 364/413.07; 364/554; 395/924
[58] Field of Search .......... 364/496, 497, 498, 413.07, 364/413.08, 413.09, 485, 554, 555; 395/924, 23

[56] References Cited

U.S. PATENT DOCUMENTS

| | | | |
|---|---|---|---|
| 4,420,384 | 12/1983 | Fujiwara | 364/498 |
| 4,742,458 | 5/1988 | Nathans et al. | 364/413.06 |
| 4,802,101 | 1/1989 | Hara | 364/413.01 |
| 4,837,726 | 6/1989 | Hunkapiller | 364/498 |
| 4,885,696 | 12/1989 | Hara | 364/413.01 |
| 4,972,325 | 11/1990 | Hara | 364/413.01 |
| 5,119,316 | 6/1992 | Dam et al. | 364/498 |
| 5,121,443 | 6/1992 | Tomlinson | 364/498 |
| 5,218,529 | 6/1993 | Meyer et al. | 364/413.01 |

OTHER PUBLICATIONS

Sanger et al., "DNA Sequencing with Chain-Terminating Inhibitors," Proceedings of National Academy of Science: Biochemistry vol. 74, No. 12 1977, pp. 5463–5467.
Maxam et al. "A New Method for Sequencing DNA," Proc. Natl. Acad. Sci., Biochemistry, vol. 74, No. 2, Feb. 1977, pp. 560–564.
Watson, et al., *The Molecular Biology of the Gene*, Benjamin/Cummings Publ. 4th Ed. 1987, pp. 274–277.

*Primary Examiner*—Jack B. Harvey
*Assistant Examiner*—Jae H. Choi
*Attorney, Agent, or Firm*—Needle & Rosenberg

[57] ABSTRACT

A method and system for automated nucleic acid sequence determination of a polynucleotide, wherein a nucleic acid sequencing ladder comprises signals corresponding to oligonucleotides formed from the polynucleotide, comprising the step of correlating, particularly in a trained neural network or a scatter plot, an intensity variable for each signal in the nucleic acid sequencing ladder with an informative variable for that signal, wherein the informative variable comprises information from at least two adjacent signals in the nucleic acid sequencing ladder, such that each signal in the nucleic acid sequencing ladder identified so as to determine the nucleic acid sequence corresponding to the polynucleotide. In particular, the relative separation between consecutive signals, the relative intensities between consecutive signals, and a pattern recognition factor, which incorporates a comparison of relative separations and intensities of at least two adjacent signals with pattern recognition templates, can be used as informative variables. Furthermore, this invention relates to a method and system for the on-the-fly resolution and extraction of information of signals contained in a digitized data stream involving calculation of the smoothed second derivative of a data point from the smoothed first derivative of the data point.

38 Claims, 16 Drawing Sheets

(extended)

5' ---T-T-A-C-G-C-C-A-G-C-T-G-G-C-G   3'

(compressed)

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: circular ( i i ) MOLECULE TYPE: DNA (genomic)

(vi) ORIGINAL SOURCE:
    (A) ORGANISM: Bacteriophage M13 mp18

(ix) FEATURE:
    (A) NAME/KEY: stemloop
    (B) LOCATION: 4..15

(xi) SEQUENCE DESCRIPTION: SEQ ID NO:1:

TTACGCCAGC TGGCG 15

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: circular (ii) MOLECULE TYPE: DNA (genomic)

(vi) ORIGINAL SOURCE:
        (A) ORGANISM: Bacteriophage M13 mp18

(xi) SEQUENCE DESCRIPTION: SEQ ID NO:2:

TAATCATGGT CATAGCTGTT 20

METHOD AND APPARATUS FOR AUTOMATIC NUCLEIC ACID SEQUENCE DETERMINATION

BACKGROUND OF THE INVENTION

The present invention relates to the automated determination of the nucleic acid sequence of a polynucleotide. More particularly, the invention relates to an improved method and apparatus for determining the sequence of a nucleic acid, particularly DNA, that utilizes novel informative variables related to the nucleic acid sequence and an associated method and apparatus that improves the resolution of nucleic acid signals in the digitized data stream corresponding to the sequencing ladder.

Current methods of DNA sequencing rely upon electrophoretic separation of incremental oligonucleotides. These stochastic arrays of oligomers are produced usually by one of two methods. The Maxam-Gilbert method (*Proc. Natl. Acad. Sci. USA*, 74: 560–564 (1977)) is a chemical method used to randomly cleave the DNA strand while the Sanger et al. method (*Proc. Natl. Acad. Sci USA*, 74: 5463–5467 (1977) uses dideoxy terminators to halt the biosynthesis process of replication.

The prior art determinants of DNA sequence have been the spatial ordering of oligomers and/or the use of differential labels with basecalling accomplished in a deterministic manner using these indicators at particular points. Thus, each base was identified individually, apart from its neighbors. For instance, one conventional approach is to monitor the signal data stream and flag the system when the signal value suddenly starts decreasing as it passes through a maximum. Therefore, by locating successive maxima, the areas in the region of each successive signal can be located. A property related to the differential label, such as the ratio of fluorescence in the region of the maxima between more than one different channel, can then be used to identify the particular base located at the end of the oligonucleotide corresponding to the particular signal. However, this method suffers not only from the possibility of not locating successive peaks, but also from problems related to inaccurate background subtraction.

The instrumental design and operation of DNA sequencers varies from simple to elaborate. Yet a fundamental limitation of each of these systems is imposed by the separation and resolution of oligonucleotides through electrophoresis in DNA sequencing gels, such as denaturing polyacrylamide gels. The system of gel electrophoresis supports determination of DNA sequences from a single sample over a range from one to hundreds of nucleotides.

The manual, autoradiographic approach to the separation of oligonucleotides presents a static view of oligomer ladders after a fixed period of electrophoresis. Recently introduced, automated DNA sequencers enable real-time detection of oligomers by recording the signal emanating from the oligomer's fluorescent or radioactive labels as each oligomer of a sequencing ladder passes the instrument's detector(s).

Automation of the separation, data collection and analysis promises efficient and rapid operation and elimination of human errors in the transcription of results to DNA sequence files. Under ideal conditions of separation and resolution of the oligomers, the identification of successive terminal nucleotides is a straightforward exercise. Many DNA sequences, however, present local domains of anomalous oligomer yields or separations. Thus, errors in manual or automated DNA sequencing files are much more likely when either the separations of oligomers, the ratio of signal to noise, or both, are sub-optimal for trivial translation of the data. These errors appear as miscalled bases, extra or missing bases, or ambiguous and unidentified bases in the DNA sequence file.

Typical performance with contemporary automated DNA sequencing systems and the scanner/readers for sequencing gel autoradiograms is on the order of 90% to 97% correctly identified bases in any single sequencing run. For any particular DNA sequence, however, this level of performance, with automated data acquisition and translation, is seldom much worse than the results of a manual DNA sequencing analysis. The automated systems reliably generate data of comparable quality in less time, with less labor intensive effort, and with lower quantities of costly reagents.

Single strand error rates of 1% are often accepted as tolerable DNA sequencing performance because comparison with complementary strand sequence data should reduce the error rate to about 1 per 10,000 base pairs. However, this accuracy is feasible only if each mismatch of sequence and complement is correctly recognized and correctly reconciled. Even then, error rates of 0.10% to 0.01% are in the range of one mistaken base per gene. This error rates approximates the level of variation among alleles of a gene pool, some of which may correlate with severe burdens of inherited pathology.

In practice, comparisons of complementary single strands with error rates of 1% initially present about 1 mismatch per 50 base pairs, necessitating the identification and reconciliation of many sequence mismatches by the professional investigator. Practical experience of many investigators, over several years of manual DNA sequencing, indicates that the reconciliation of complementary strand mismatches is challenging, but feasible. The process is clearly tedious and time consuming. Furthermore, criteria for objective reconciliation of errors are not known.

Because small improvements in accuracy in the translation of raw sequencing data has a substantial impact on the level of undetected errors in the finished DNA sequences and, thus, the cost of DNA sequencing, there is a need for a method and apparatus to improve the accuracy of the finished DNA sequences. The instant invention solves this problem by providing methods and apparatus for both the enhanced separation and resolution of signals emanating from the labeled oligonucleotides and the improved determination of nucleic acid sequence employing novel informative variables related to the local nucleic acid sequence.

SUMMARY OF THE INVENTION

The present invention relates to the discovery and implementation of novel informative variables that contain information relating to the nucleic acid sequence and a process for extracting information on-the-fly from a digitized data stream that corresponds to the nucleic acid sequencing ladder. Because the novel informative variables contain information concerning the identity of neighboring nucleotides in a polynucleotide, these variables can be combined with the prior art determinants of nucleic acid sequence to obtain improved accuracy, approaching 100%, in basecalling. Furthermore, the on-the-fly process for resolving signals provided by this invention allows for more accurate detection of the characteristics of signals in a nucleic acid sequencing ladder, thus providing a method and system for accurately measuring these novel informative variables. Because the measurement and correlation of these variables are suitable for processing in a computer, this invention discloses a method and system for automated nucleic acid sequence determination for a polynucleotide, such as DNA, RNA and the like.

More particularly, this invention provides a method and system for automated nucleic acid sequence determination in which an intensity variable for each signal in the nucleic acid sequencing ladder is correlated with an informative variable for that signal such that each signal in the nucleic acid sequencing ladder is identified to determine the nucleic acid sequence corresponding to the polynucleotide. The informative variable is a variable that comprises information from at least two adjacent signals in the nucleic acid sequencing ladder, such as the relative separation between two consecutive signals, the relative intensity between two consecutive signals, or a combination of intensity and separations for at least two adjacent signals. The intensity variable is the intensity of a signal or a variable formulated from the intensity of that signal, including the ratio of the intensities obtained from two different data streams for the same signal.

The electrophoretic separation of oligonucleotides in nucleic acid sequencing gels is primarily a function of length. However, as disclosed by this invention, the terminal nucleotides of an oligomer affect that oligomer's mobility in a determinable fashion. Thus, the relative separation between adjacent signals, as determined for a particular signal in a nucleic acid sequencing ladder, contains information regarding the identity of terminal nucleotides, particularly the last 2–3 nucleotides, of the oligomer that corresponds to that particular signal in the sequencing ladder. Thus, the use of the relative separation informative variable, particularly in conjunction with prior art determinants of nucleic acid sequence, such as spatial ordering and/or the use of differential labels, provides for improved nucleic acid basecalling.

Furthermore, the yield of a particular oligomer, which correlates to the intensity of the signal in the sequencing ladder that corresponds to that oligomer, is dependent upon the affinity of base incorporation by the polymerase during replication. As shown by the instant invention, relative oligomer yields are determined by competition between pools of deoxynucleotides and dideoxyterminators in a manner that is dependent upon the nucleic acid sequence in the immediate locale of the nucleic acid chain elongation. Thus, the use of relative intensities as an informative variable for a particular signal, particularly in conjunction with prior art determinants of nucleic acid sequence for that signal, provides for improved nucleic acid basecalling.

Because information contained in a sequencing ladder signal corresponding to a particular oligomer contains information regarding the identity of neighboring oligomers, the instant invention provides for the use of a combination of variables, such as relative separations, relative intensities, intensities and the like to provide information regarding the identity of the terminal nucleotide of a particular oligomer from neighboring signals. Thus, the pattern array of the sequencing ladder contains information regarding the nucleic acid sequence. Thus, comparison of relative separations and intensities of at least two adjacent signals with a multiplicity of pattern recognition templates, which comparison can be expressed as a pattern recognition factor, provides information regarding the sequence of a nucleotide and can be used to improve basecalling. Alternatively, intensities, relative intensities, relative separations and the like for signals from a sequencing ladder can be imputted into a trained neural network to obtain accurate sequence designations for a nucleotide.

All of the above-mentioned variables can be correlated, either singly or in combination, to provide finished nucleic acid sequences, such as in a rule-based expert system or a trained neural network. Furthermore, because the acquisition and correlation of these variables is ideally suited for processing in a computer, this invention also provides for systems for automated nucleic acid sequence determination comprising means for calculating an intensity variable, means for calculating an informative variable and means for correlating the intensity of each signal with the informative variable for each signal.

In order to obtain accurate measurement for the variables used to determine nucleic acid sequence information according to the present invention, this invention provides a method and system for enhanced resolution of signals contained in a digitized data stream comprising successive signals corresponding to oligonucleotides in a nucleic acid sequencing ladder formed from a nucleotide. According to this method, the second derivative smoothed over m data points of the first derivative smoothed over n data points for a particular point in the digitized data stream is calculated from the $n+m+1$ data points of the digitized data stream. Each second derivative value that is positive is replaced by zero and each second derivative value that is negative is multiplied by $-1$ to produce a second digitized data stream in which the signals are clearly separated by at least one zero, the maxima of the various signals are easily detected, and integration of the signals to obtain intensities is trivial. This rapid, time-linear, incremental process for extracting features from a data stream can be easily adapted for on-line computer analysis or implementation in a semiconductor chip; thus, the instant invention provides for a system for rapid on-the-fly resolution of signals contained in a digitized data stream. Because this time-linear process provides for rapid data processing, this method is also ideally suited in contexts other than nucleic acid sequencing, such as time-of-flight mass spectrometry.

Thus, an object of this invention is to provide a method for nucleic acid, particularly DNA, sequence determination of a nucleotide by correlating an intensity variable for each signal in a nucleic acid sequencing ladder with an informative variable for that signal, wherein the informative variable comprises information from at least two adjacent signals in the nucleic acid sequencing ladder. The use of relative separation, relative intensity and a pattern recognition factor as informative variables in this method, either singly or in combination, are explicit objects of this invention. It is a further object of this invention to correlate the intensity variable with the informative variable(s) through use of a rule-based expert system, formulation of a scatter plot or input of data into a trained neural network.

A further object of this invention is to provide a system for the automated nucleic acid sequence determination of a polynucleotide from a digitized data stream in which the data stream comprises successive signals corresponding to oligonucleotides in a nucleic acid sequencing ladder formed from a polynucleotide. Thus, it is an object of this invention to provide a system including means for calculating an intensity variable for each signal in the digitized data stream, means for calculating an informative variable for each signal, and means for correlating the intensity for each signal with the informative variable, most preferably in conjunction with means for obtaining the digitized data stream and memory means associated with the calculating means.

In addition, it is an object of this invention to provide a process and a system for the on-the-fly resolution of signals contained in a digitized data stream to produce partially resolved signals. This process and system relate to obtaining, from $n+m+1$ data points, a smoothed second derivative from the smoothed first derivative for each point in the data stream. It is a particular object to provide a method and system that can extract features rapidly, on-the-fly from a data stream.

BRIEF DESCRIPTION OF THE FIGURES

FIG. 2 shows results of the electrophoresis of an M13 mp18 DNA sequencing ladder at 750 volts.

FIG. 3 shows relative separations (dimensionless) for successivive oligonucleotides taken from FIG. 2B evaluated by dividing the separations of successive oligonucleotides by the average separation function of oligomer length.

DETAILED DESCRIPTION OF THE INVENTION

Separation of Oligonucleotides

Figure 1A:
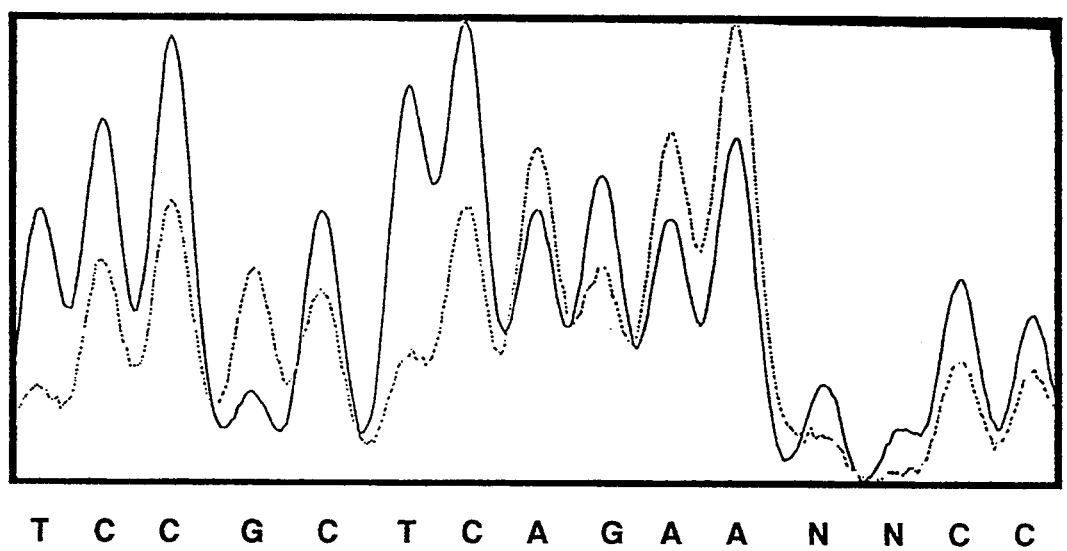
FIG. 1 shows a comparison of a fifteen-base DNA digitized data stream obtained from a Du Pont Genesis 2000 ™ automated DNA sequencing unit with the same data treated with the second derivative on-the-fly process for facilitating peak finding and analysis of the instant invention.

Current methods of DNA sequencing rely upon electrophoretic separation of incremental oligonucleotides. Two basic approaches are usually employed to create these sequence-specific oligomer distributions. The strategy devised by Maxam & Gilbert employs nucleotide-specific chemical cleavages of labeled DNA restriction fragments. The biochemical strategy of Sanger et al. employs base-specific termination of 5' primer-initiated, in vitro DNA synthesis on complementary DNA templates. However, oligomer ladders generated either by the chemical cleavage method, the biochemical strategy or other methods are suitable in the pattern-recognition, expert system of the instant invention.

Furthermore, any suitable method can be used to label the oligonucleotides so as to allow correlation of a particular oligonucleotide with a particular terminal base. For instance, radioactive nucleotides, such as $^{32}P$ or $^{35}S$, can be used to label the oligomers of DNA sequencing ladders. Following electrophoretic separation of the oligomers, methods such as autoradiography or on-line analysis of the electrophoretic separations of the radiolableled nucleotides can be used to record the distribution of the products of sequencing ladders.

Furthermore, the DNA fragments can be tagged with fluorescent labels, such as fluoroscein labels. These labels can be placed at either the 5' or 3' ends of the oligomers and can be used in automated DNA sequencing instruments. These instruments monitor electrophoresis in real-time and provide a temporal record of the successive oligomers as they pass a fixed position detector. Because these labels can be attached to the dideoxy terminators used to halt the replication process, the biochemical strategy predominates in these applications.

In addition, it is possible to employ mass spectrometry-based detectors to monitor oligomers labeled with stable isotopes of sulfur or metals, such as Fe or Sn. This method offers increased sensitivity, improved discrimination among different labels, and more rapid data generation.

Any technique capable of separating the oligonucleotide fragments can be used. However, with minor modifications, the denaturing polyacrylamide gel system is the preferred system. Incremental separation of the oligomers by length typically supports analysis up to 200 to 500 bases in a sequencing ladder. Deliberate variation of field strength and direction during electrophoresis (FIGE, etc.) can dramatically extend the range of separations for large double-stranded DNA molecules in agarose gels. Capillary gels and ultra thin gels offer reduced Joule heating of a gel subjected to higher fields and, thus, greater resolution of the oligonucleotides in less time compared with conventional DNA sequencing gels.

Typically, the manual, autoradiographic approach with radioactive nucleotides relies upon the physical segregation of the sample into four separate parallel sub-ladders, each set of oligomers corresponding to one of four possible terminal nucleotides. The physical position (lateral) of each oligomer's sub-ladder is the indicator of the identity of its terminal nucleotide. The exposure patterns on the gel autoradiograms can be scanned, such as with automated scanning densitometers, to allow translation of the information to a digitized data stream such that each sub-ladder is digitized separately or all four sub-ladders are superimposed in a digitized data stream corresponding to the oligomer ladder.

The automated approach typically uses four base-specific fluorescent labels and permits all of the oligomers of a sample to be analyzed within a single lane. These automated systems, such as ABI 370 ™ (Applied Biosystems, Inc., Foster City, Calif.) and Du Pont Genesis 2000 ™ (Du Pont, Wilmington, Del.), incorporate hardware design and software to differentiate the four labels as successive oligomers of the ladder pass the detector, such as a fixed position laser scanner detector, preferably a dual filter, dual photometer laser scanning system. The signals corresponding to the oligomer ladder can then be converted into a digitized data stream.

The following example is illustrative of the separation procedure and is not meant to limit the instant invention.

A DuPont Genesis 2000 ™ automated DNA sequencing unit was used to process samples of DNA from phage M13mp18. Sequencing primers were prepared using NEN/Du Pont phosphoramidite reagents and solvents with a Du Pont Generator ™ single-column oligonucleotide synthesizer. Primers were eluted from columns and purified by denaturing polyacrylamide gel electrophoresis, prior to use in sequencing reactions.

DNA sequencing kits for single-stranded template reactions, employing succinyl fluoroscein-labeled dideoxynucleotides, deoxynucleotides, reaction buffer and Sequenase ™ were obtained from NEN/Du Pont. These kits, which are available in convenient tablet form, are based on routine sequencing reactions. Reaction conditions are easily modified to include $MnCl_2$ at 2 mM. All sequencing reactions include both $C^7$-deaza dGTP and $C^7$-deaza dATP to improve the uniformity of mobility and chain length in the product DNA sequencing ladders.

Electrophoresis was performed though 6% or 8% polyacrylamide gels (19:1 monomer to bis; 0.4 mm×370 mm×125 mm), containing 8M urea, buffered with 0.1M Tris-borate, pH 8.8, 1 MM $Na_2EDTA$. Gels were exhaustively prerun (2 to 3 hours at 1000 volts) to constant resistance of 100,000 ohm, prior to loading of the DNA samples. The gel electrophoresis of DNA samples was performed at constant voltage, 750 V, typically over a period of about 18 hours.

The SF-505 succinyl fluoroscein fluorophore was attached via a phosphoramidite to the 5' end of an oligonucleotide representing all but the last base of the M13 mp universal sequencing primer. The usual 3' fluorophore-labeled dideoxynucleotide terminators were replaced with 0.075 mM unlabeled dideoxynucleotides ddGTP, ddATP, ddCTP and ddTTP (Pharmacia). The terminators were present either individually in the reactions to generate sample lane-specific 3' dideoxynucleotide ladders or all four together to generate a singly labeled, complete sequencing ladder in one lane. The fluorescence ratios of these 5'-labeled oligomer ladders were uniformly representative of the SF-505 succinyl fluoroscein fluorophore.

Figure 10:
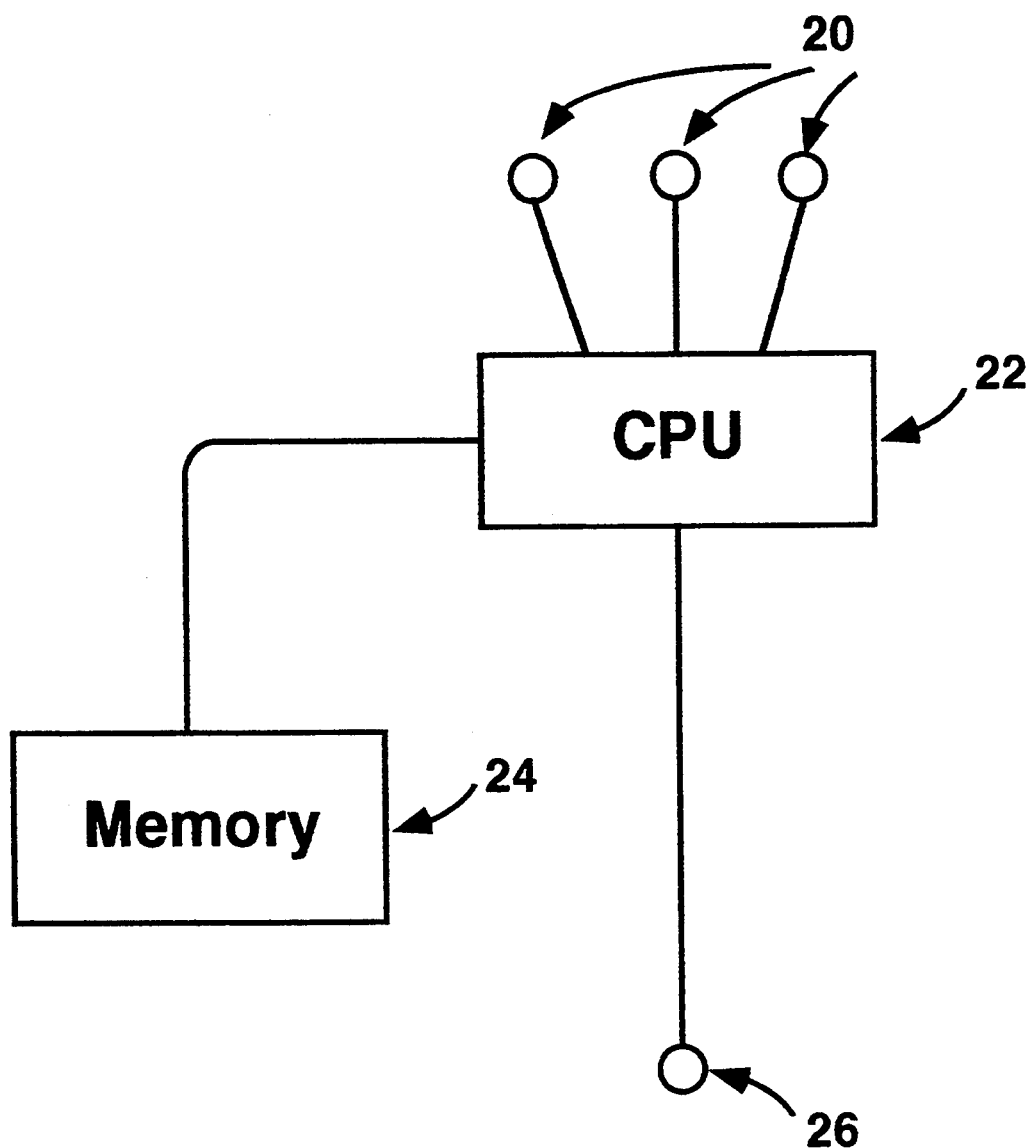
FIG. 10 shows a means for calculating the different parameters and a memory means associated with the calculating means.

Genesis ™ 2000 instrument control, data acquisition and analysis according to the instant invention were performed using an Apple Macintosh II computer. As seen in the schematic diagram of FIG. 10, the intensity and other informative variables are acquired through data inputs 20 and correlated in a calculating means 22 which is also attached to a memory means 24, allowing the determination of nucleic acids which is reported by the data outputs 26. The 7 cm detector window of the Genesis ™ 2000 was repetitively scanned as 90 horizontal steps, at intervals of 6.7 seconds, over 18 hours of electrophoresis. Under these conditions successive oligomers are separated by 10 to 30 scan intervals, peak to peak, throughout the run. The elapsed time (from the computer's internal clock) and the digitized fluorescence output from the photometers (output channels, PMT-A and PMT-B) of the Genesis ™ 2000 were recorded for each scan, from the time of sample loading until the end of the run. Typical raw data files occupy about 2 to 3 Mbytes of computer memory in binary format.

Data corresponding to single DNA sample lanes was integrated by summation of the raw photometer signals of each scan over three to five adjacent scanner positions. This procedure typically increases the total signal from each photometer about 2.3 fold compared with data collected in a single scanner track as a cross section and results in approximately 50% improvement in signal to noise under these conditions.

Enhanced Resolution of Signals in the Raw Data Stream

As discussed above, prior art methods of detecting signals in the raw data stream suffer from inaccuracies in the extraction of signal positions, separations and intensities. However, the instant invention provides a method and apparatus for enhancing the separation and resolution of signals in the raw data stream.

According to the instant invention, the identification of the positions of the maxima of successive signals in a digitized data stream (having values $A_1$ to $A_N$ for N points in the data stream) can be obtained on-the-fly and without having to curve-fit the signals in the data stream to models. As used herein, the term "positions of the maxima" or "position of the maximum" or the like refers to either the temporal position of a maximum in a data stream digitized in time units or the spacial position of a maximum in a data stream digitized in distance units.

First, the first derivative for the first data point is calculated from two successive data points, $A_2-A_1$. However, to smooth this derivative and reduce the noise that may have been introduced by this procedure, the smoothed first derivative at this point is calculated by taking an average or taking a running sum of the differences for n points in a row. For instance, using three points in a row, the smoothed first derivative for the first data point can be given as $(A_4-A_3)+(A_3-A_2)+(A_2-A_1)=A_4-A_1$. Thus, the smoothed first derivative can be calculated on-the-fly, using n+1 data points from the data stream as the data stream is accumulated, where n=the number of points the first derivative is smoothed over.

In a similar fashion, the smoothed, second derivative for the first point of the data stream can be obtained by taking the differences of differences. For example, considering n=3 and m (the number of points the second derivative is smoothed over)=3, the differences of differences for the first data point corresponds to $A_7-2A_4+A_1$. The smoothed second derivative at the second and subsequent data points can be obtained directly, by summation of smoothed differences, or by calculations from data arrays. In either case, as each new data point in the data stream is obtained, it is possible to almost immediately calculate from a small array (n+m+1 points) the smoothed second derivative of the smoothed first derivative, thus avoiding the long time otherwise required for curve-fitting or peak shape/overlap analysis. Typically, n or m range from 2-25, preferably 2-12, most preferably 2-6 points. Obviously, as the number of data points defining a signal increases, n or m can increase.

Because the negative values for the second derivative profile correspond to regions in the original data stream near the maximum of each peak, the minimum of the second derivative signals occur in time at precisely the same point as the maximum in the original curve. The points where the second derivative curve crosses zero correspond to the inflection points, at the rising and falling side of each peak in the signal stream.

Thus, by truncating all the positive values in the smoothed second derivative curve and multiplying the remaining second derivative values by $-1$, the resulting curve portrays a clean, segregated set of peaks in which each contiguous array of positive points represents a peak that is separated from the next peak by one or more zeros. Each peak represents data selected only from the best region of the corresponding signal in the data stream. This procedure allows for calculation of the highest point of a signal with the minimum overlap from the preceding and following signals that might not be totally resolved from the center signal in the original data stream.

Integration of these peaks in the smoothed, second derivative curve is trivial; that is, integration simply involves looking for zero values that suddenly go positive and taking the sum of all the positive values until two or three zero values in a row are encountered. Thus, the intensity of a signal, or a variable formulated from the intensity, such as the ratio of the intensities obtained from two different data streams for the same signal or some function of this ratio, such as the natural log of this ratio or the differences of the intensities in both streams divided by the sum of the intensities in both streams, can be obtained easily. For instance, in the nucleic acid sequencing context, the intensity of a signal from one data channel corresponds to the yield of a particular oligomer and the natural log of the ratio of the intensities of a signal from two data channels is typically related to the identity of the label attached to that oligomer. As used herein, the term "intensity variable" refers to the intensity of a signal in a data stream or a variable formulated as discussed above for that signal.

By integrating these smoothed, second derivative peaks and multiplying each peak times the time, it is possible to calculate the first moment of time. Division of the sum of these time-signal products by the sum of signals allows the calculation, to literally a tenth of a second out of tenths of thousands of a second, the exact time of passage of each peak as it passes the detector.

As a test of this rapid, time-linear process for facilitating peak finding and analysis, a raw data stream from the analysis of a DNA fragment, processed as described above through the Du Pont Genesis 2000 ™ automated DNA sequencing unit, was treated with the above peak finding process before being fed to the Du Pont commercial base-calling software, which determines the DNA sequence by using the ratio of fluorescence through two channels only. Data treated in this fashion resulted in fewer base-calling errors or ambiguous calls relative to the raw data.

Figure 1B:
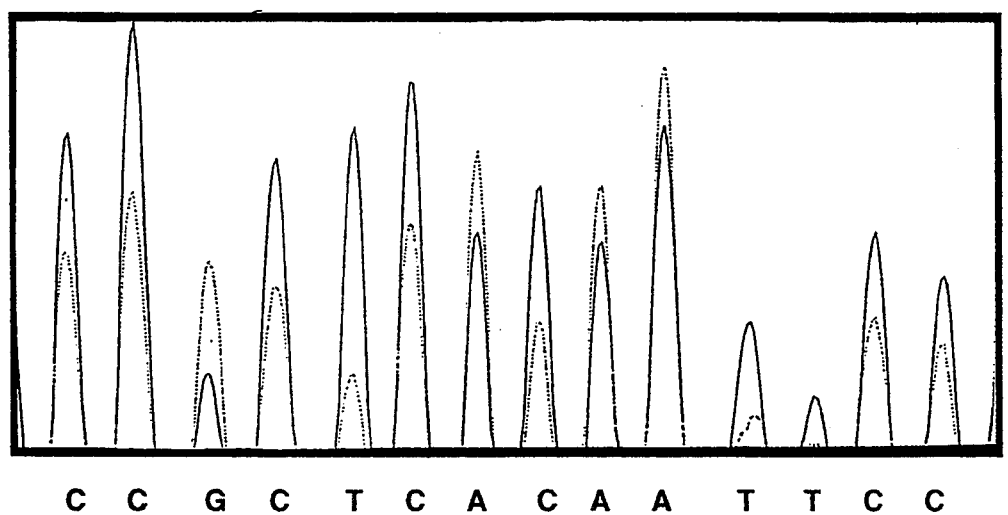

FIG. 1 shows DNA sequence ladder waveforms from two photometer data streams of a Du Pont Genesis 2000 ™ automated sequencer. FIG. 1A reflects data generated directly by the instrument while FIG. 1B represents the same data transformed by the time linear second derivative-based process to deconvolve the peak events and facilitate review for base-calling. Fifteen oligomers are identified in each panel, but prior to transformation, only 13 are correctly specified in the DNA sequence.

Thus, the on-the-fly second derivative procedure does not destroy the fluorescence spectrochemical integrity that allows primary identification of the various bases. However, in addition to treating the fluorescence labeling of signals correctly, this time linear procedure provides the exact time of electrophoretic elution for each signal (peak) in the data stream (i.e., the position of the maximum) and, thus, precise differences between successive peaks. As is discussed below, this precision is important because it allows extraction of more accurate signal separations and intensities, which are necessary for both expert system and pattern recognition based approaches for basecalling.

Thus, with no elaborate calculations, this second derivative method provides a very rapid way of extracting signals out of a data stream and minimizing the peak-to-peak loss from contamination or evaluation. This time-linear evaluation of smoothed second derivatives of the primary data streams provides partially deconvolved arrays of fluorescence and mobility data for sequences of oligomers in the nucleic acid sequencing context. Furthermore, this method is also very effective in a wide variety of applications beyond DNA sequencing analysis, particularly in applications in which resolution on-the-fly of a digitized data stream corresponding to partially overlapping signals is desired. Because this method is capable of facilitating peak finding and analysis, partially deconvoluting incompletely resolved peaks, recording peaks as events associated with times of detection and signal intensities, circumventing quantitative problems associated with estimation of background and providing a signal stream that is more easily interpreted by visual scanning, this method can be used for enhanced resolution of signals in many contexts, including component analysis in chromatography, mass spectrometry, digital imaging and image processing instrumentation.

This method is particularly applicable to time-of-flight mass spectrometry because it is capable of extracting signals from a raw data stream on-the-fly. For instance, in the isotopic analysis of metals such as tin or chromium, data acquisition is on the order of 10 to 100 $\mu$sec per full scan with recycling occurring at a rate of 50 to 100 times a second. Thus, the rapid processing of the instant invention allows for extraction of the relative amounts of the various isotopes rapidly and accurately, thus avoiding the cumbersome curve-fitting processes otherwise necessary.

Use of Electrophoretic Separations Between Successive Oligomers as an Informative Variable in Nucleic Acid Sequencing The instant invention provides for an improved method and apparatus for nucleic acid sequencing by identifying and implementing new informative components of nucleic acid sequencing ladders in addition to the primary determinative variables such as lane position or fluorescence ratios. One such informative variable is the relative separations of successive oligomers in the nucleic acid sequencing ladders. As used herein, the term "relative separation(s)" for an adjacent pair of oligomers refers to either the spatial distance between the successive or adjacent signal maxima in a static view of an oligomer ladder or the temporal distance between the successive or adjacent signal maxima as they pass by a detector divided by either the expected average spatial distance or expected average temporal distance, respectively, on based length.

Electrophoretic separation of oligonucleotides in nucleic acid sequencing gels, such as denaturing polyacrylamide gels, is primarily a function of length-dependent mobility. However, as is described in our paper, "Neighboring Nucleotide Interaction During DNA Sequencing Gel Electrophoresis", *Nucleic Acids Res.*, 19: 3089–3097 (1991), the contents of which are incorporated by reference, the 3' terminal nucleotide sequence of the oligonucleotide is a significant, secondary determinant of mobility and separation.

Compression artifacts are striking anomalies of oligonucleotide separations in DNA sequencing ladders. The mobilities of compression-prone oligomers are not uniformly related to their relative lengths and, thus, this compromises local sequence determination. Compressions are generally attributed to idiosyncratic DNA sequences, prone to form secondary structures such as hairpins or stem-loops even in the denaturing environment of 7 to 8M urea. Electrophoresis at elevated temperatures can often restore compression-prone sequences to more uniform order in the ladder with respect to oligomer length. Purine deoxynucleotide analogues have also been used, during the DNA synthesis stage of sequencing, to provide products with reduced propensity to exhibit compression artifacts. Complementary strand sequence determinations often provide unambiguous results through regions compressed in the first strand's ladder. However, none of these approaches to dealing with mobility artifacts is universally applicable with satisfactory results.

The instant invention discloses the discovery of a more subtle, but at the same time more pervasive anomaly of the electrophoretic separations of oligonucleotides. The temporal separations of successive oligomers are observed to vary extensively from oligomer to oligomer in a typical DNA sequencing ladder. However, the major determinant of this variance of separation is the 3' terminal DNA sequence of two to three nucleotides.

The manual, autoradiographic approach to DNA sequencing presents a static view of oligomer ladders after a fixed period of electrophoresis. Mobility differences of oligomers are determined from their relative distances of migration from the loading well. This method has the disadvantage that longer oligomers traverse shorter distances and are physically closer to their immediately shorter or longer neighbors. Recently introduced, automated DNA sequencers enable real-time detection of oligomers as they pass a fixed position in the gel. Mobility differences, in this case, are evaluated from the differences in time required for electrophoretic transport over a fixed distance from the loading well. The average temporal separations of oligomers are more uniform, over the range of oligomer lengths in a typical sequencing ladder, than are the average physical separations of the oligomers determined from a static view. Otherwise, the factors affecting the mobilities of oligonucleotides during gel electrophoresis are identical for the manual, static view approach and the automated, real-time approach.

Samples of DNA from phage M13 mp18, or spontaneous or induced mutants, were sequenced using the dideoxynucleotide chain termination strategy and protocols developed for the fluorescence-based Du Pont Genesis TM 2000 automated DNA analysis system.

Fluorescent labeling of DNA sequencing ladders with 3'-labeled terminators was accomplished as follows. Annealing of template, 3 $\mu$g M13 phage DNA, and 15 ng universal primer (the 17-mer from $-40$) was performed in 20 $\mu$l, 65 mM Tris-HCl, pH 7.5, 80 mM NaCl, 32 mM MgCl$_2$ by heating 5 min at 95° C., followed by incubation for 10 to 20 min at 37° C. DNA synthesis followed using the annealed primer-template DNA and 3 to 6 units of Sequenase TM (United States Biochemical Corp.) in a single tube as 30 $\mu$l, with 47 mM Tris-HCL, pH 7.5, 59 mM NaCl, 23 mM MgCl$_2$, 2 mM MnCl$_2$ and 8 mM dithiothreitol: C$^7$-deaza-dGTP, C$^7$-deaza-dATP, dCTP and dTTP were each present at 7.5 $\mu$M; the 3' dideoxy terminators were included as 0.075 $\mu$M ddGTP-505, 0.15 $\mu$M ddATP-512, 0.15 $\mu$M ddCTP-519 and 0.30 $\mu$M ddTTP-526. All nucleotides used were components of NEN-Du Pont Genesis TM system DNA sequencing kits. After 10 min at 37° C., 30 $\mu$l of 5M ammonium acetate, pH 7 and 150 $\mu$l of cold ethanol were added to precipitate the DNA. After washing the pellet once with cold 70% ethanol, the dried pellet was dissolved in 6 $\mu$l 95% formamide, 5 mM Na$_2$EDTA, pH 8, then heated 5 min at 95° C. One half of the sample was then loaded into a single well of the gel for electrophoresis.

Fluorescent labeling of DNA sequencing ladders with 5' labeled primer was accomplished as follows: Fluorophore-labeled oligomers were developed by Du Pont for lane tracking in the operation of the Genesis TM 2000 automated DNA analysis system. The SF-505 succinyl fluorescein fluorophore was attached via a phosphoramidite to the 5' end of an oligonucleotide representing all but the last base of the universal sequencing primer. This labeled oligomer was provided by George Tice (Du Pont, Glasgow, Del). The same annealing conditions were employed as described above, using 3 $\mu$l of the 5' labeled primer (diluted 1:10000, estimated 15 ng). For DNA synthesis, the conditions were also the same as described above, except the 3-labeled dideoxynucleotide terminators were replaced by the unlabeled dideoxynucleotides ddGTP, ddATP, ddCTP and ddTTP (Pharmacia), 0.075 $\mu$M each. Identification of the oligonucleotides in these uniformly labeled ladders was straightforward, by comparisons with four parallel ladders in which samples were prepared by inclusion of only one of the four terminators. The fluorescence ratios of these 5'-labeled oligomer ladders were uniformly representative of the SF-505 succinyl fluoroscein fluorophore.

Electrophoresis was performed through 7% polyacrylamide gels (19:1 monomer to bis; 0.4 mm$\times$370 mm$\times$125 mm), containing 8M urea buffered with 0.100M Tris-borate, pH 8.8, 1 mM Na$_2$EDTA. Gels were exhaustively prerun (2 to 3 hours at 1000 volts) to constant resistance of 100,000 ohm, prior to loading. The gel electrophoresis of DNA samples was performed at constant voltage, in the range of 500 to 1500 V, depending on the experiment. Continuous temperature measurements were performed with a 4 mm diameter, flat-faced remote thermistor probe place on the surface of the outer gel plate, approximately 5 cm above the detector window. The thermistor was previously calibrated at 4° C. and 100° C. using distilled water/ice and boiling water. Typical gels run at 750 V maintained a plate surface temperature of 32° C.

Genesis TM 2000 instrument control, data acquisition and analysis were performed using an Apple Macintosh II computer. The entire 7 cm detector window of the Genesis TM 2000 was repetitively scanned as 90 horizontal steps, at intervals ranging from 4 to 10 seconds, over 6 to 48 hours of electrophoresis. The time per scan was selected to provide data separation of successive oligomers by 10 to 30 scan intervals, peak to peak, throughout the run. The elapsed time (from the computer's internal clock) and the digitized fluorescence output from the two photometers (PMT-A and PMT-B) of the Genesis TM 2000 were recorded for each scan and subsequently analyzed in spreadsheet format with graphics (Microsoft Excel v. 2.2, CricketGraph v. 1.2).

Identification of terminal nucleotides of oligomers in the sequencing ladders is based on the ratio of fluorescence (as ln(PMT-B/PMT-A)) associated with each of the base-specific terminators. The times required for electrophoresis from well to detector were evaluated by fluorescence intensity weighting of elapsed times corresponding to the four scans of maximum signals for each oligomer.

The Genesis TM 2000 DNA analysis system was used to characterize mutations in the lac Z gene, either spontaneous mutations or those induced by an activated ethylene dibromide mutagen. A specific oligonucleotide primer was synthesized for these experiments (M13 mp18 nucleotides 5'-6423 to 3'-6406, as reverse complement), to sequence through the amino-terminal coding region of the gene. This primer anneals to complementary DNA sequence of M13 mp18 template, 100 bases upstream from the conventional universal primer. ('Upstream' and 'downstream' references are given with respect to the 5' to 3' polarity of the oligomer product DNA strands.)

The Du Pont Genesis TM 2000 automated DNA sequencer permits identification of 3' dideoxynucleotide terminators on each successive oligonucleotide, based on spectral properties of four base-specific fluorophores. In the following experiments, the fluorescence measurements, together with the known DNA sequence of M13 mp18, were used to establish the length of oligomers in the DNA sequencing ladders. The instrument was programmed to simultaneously record the elapsed time of electrophoresis (seconds) with each laser-photometer scan of the detector window.

Figure 2A:
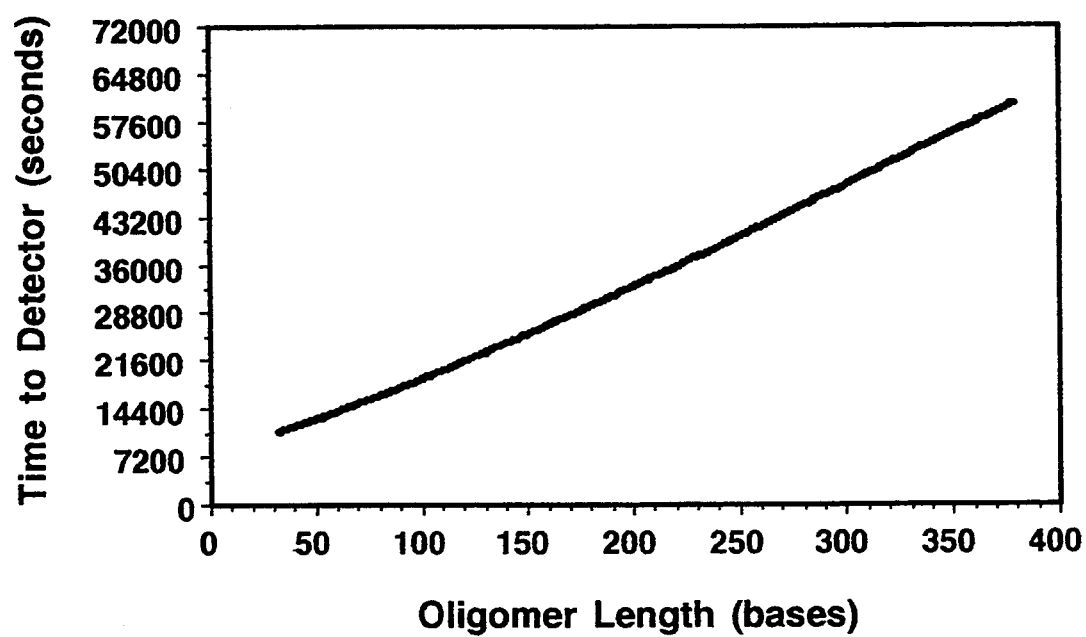
FIG. 2A shows that the time required for oligomers to traverse the gel from well to detector is a uniform and monotonic function of oligomer length.

An M13 mp18 DNA sequencing ladder undergoing electrophoresis at 750 V is analyzed in FIG. 2A, showing the uniform, nearly linear relation between the time (seconds) for electrophoresis from well to detector and the length of the oligonucleotides (bases). Linearity of this function corresponds to an inverse relationship between mobility of the oligomers and their length.

Figure 2B:
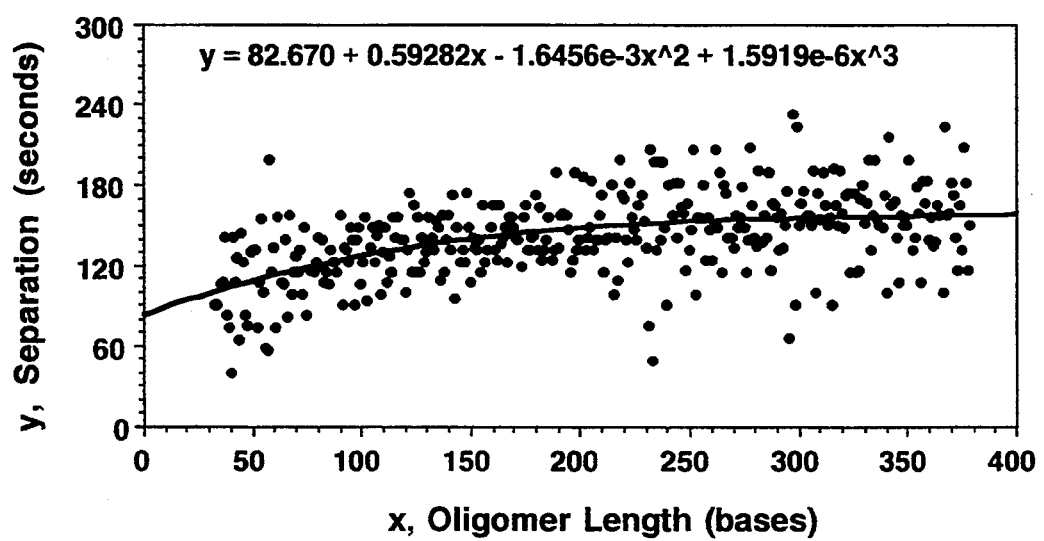
FIG. 2B shows that the separations of successive oligomers increase gradually from about 90 seconds to 150 seconds over the range of 30 to 400 nucleotides, subject to large variance throughout this range.

In this experiment, the oligonucleotides are separated by 1 to 4 minutes, peak to peak (i.e., from the position of the maximum of one signal to the position of the maximum of the successive signal), over the range of almost 400 nucleotides, FIG. 2B. The scatter of individual points indicates large variance of the temporal separation of successive oligomers throughout this range. As shown in FIG. 2B, a third order polynomial function, determined by least squares curve-fitting, was used to describe the average temporal separation as a function of oligomer length. The relative separation of any adjacent pair of oligomers, (N)-mer and (N−1)-mer, can then be expressed as the ratio of actual time between their respective maximum signals and the average time difference expected for an oligomer of length N. On transformation of the data in FIG. 2B in this manner, the entire ladder has an average relative separation 1.000±0.192 (standard deviation) as shown in Table 1. A wide interval, from 0.4 to 1.6 times the average relative separation, is required to include 99% of the oligomers.

TABLE I

| Relative Separation of Successive Oligonucleotides | | |
|---|---|---|
| 3' terminal nucleotide | Fluorophore on 3' dideoxynucleotide | Fluorophore on 5' primer |
| -ddN | 1.000 ± 0.192 (347) | 1.000 ± 0.194 (316) |
| -ddT | 1.177 ± 0.108 (85) | 1.166 ± 0.124 (79) |
| -ddG | 1.049 ± 0.150 (95) | 1.031 ± 0.173 (86) |
| -ddA | 0.959 ± 0.126 (77) | 0.966 ± 0.143 (70) |
| -ddC | 0.815 ± 0.163 (90) | 0.838 ± 0.170 (81) |

The relative separations of oligonucleotides from an M13 mp18 DNA sequencing ladder are shown as average ± standard deviation (number of events). Parallel DNA sequencing ladders were labeled with fluorescent 3' terminators or 5' primer and these provide statistically indistinguishable results. The relatively slowest species have 3' -ddT, the fastest have 3' -ddC.

The data shown in FIG. 2 were obtained using a sample prepared with fluorophore-labeled dideoxynucleotides as 3' chain terminators. Statistically identical results are obtained with DNA samples prepared using a 5' oligonucleotide primer, labeled with dG-505 fluorophore, together with unlabeled dideoxynucleotide terminators. These 5'-labeled oligomers have an average relative separation of 1.000±0.194, in parallel tracks of the same gel as shown in Table 1.

Other investigators have remarked on the uniform and monotonic decrease of mobility with oligomer length, and they have suggested this may facilitate localization of low yield oligomers in the ladder. The large variance in separations from oligomer to oligomer in DNA sequencing ladders, which we report and characterize here, may compromise the utility of such a search algorithm.

Figure 3A:
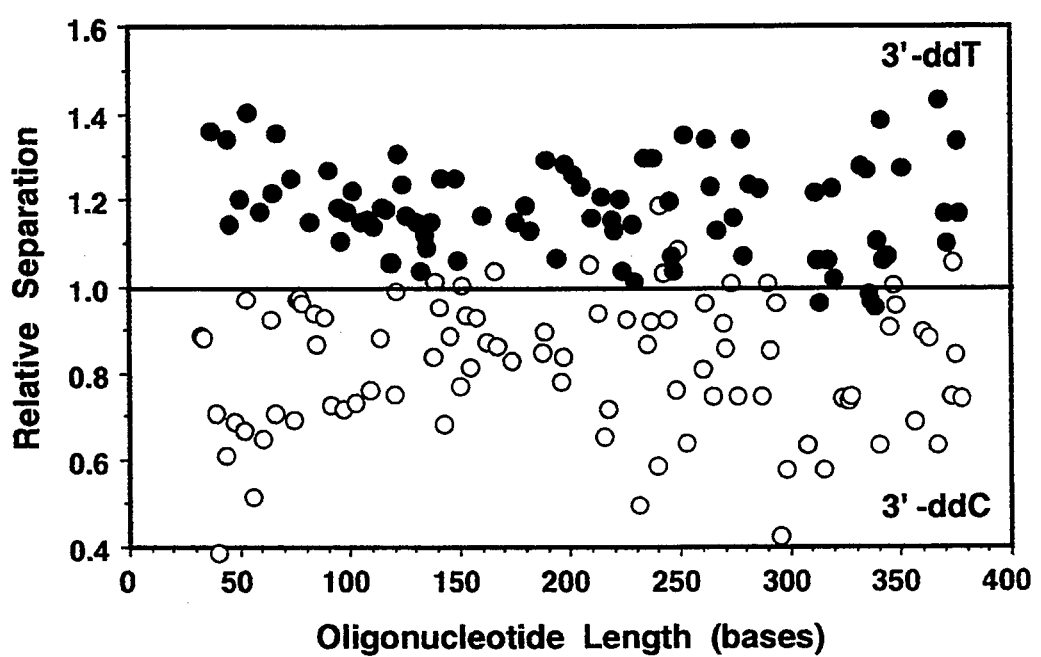
FIG. 3A shows the portion of the data set which corresponds to those oligomers with 3'-ddT-terminated oligomers (black circles, slower than average) and those oligomers which end with 3'-ddC (open circles, faster than average).
Figure 3B:
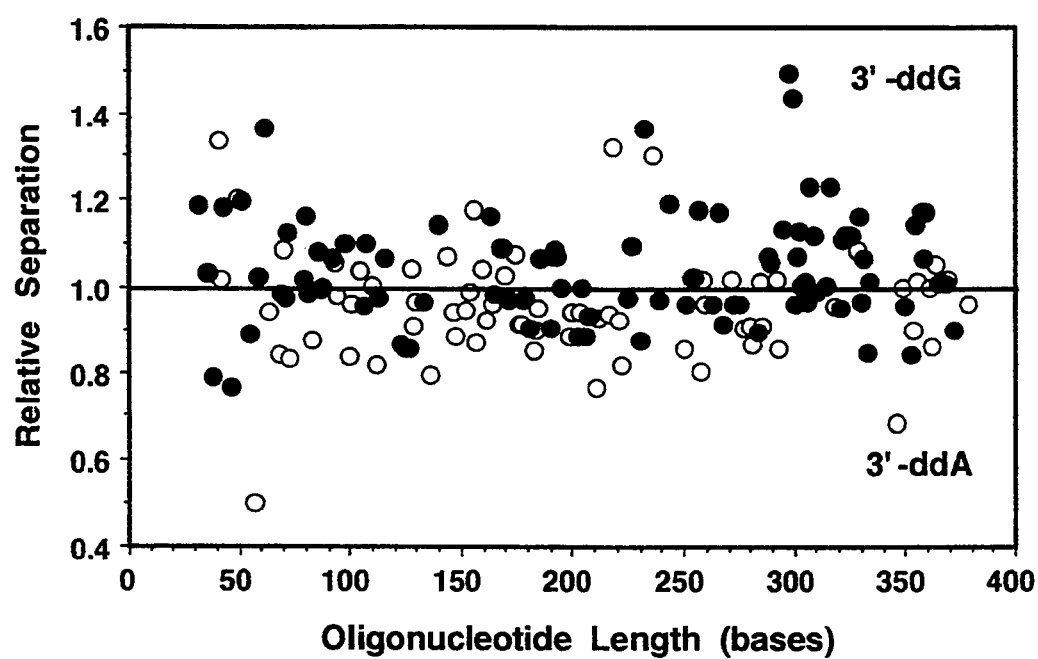
FIG. 3B shows the portion of the data set which corresponds to those oligomers with 3'-ddG-terminated oligomers (black circles, faster as a group than average) and 3'-ddA-terminated oligomers (open circles, slower than average)

Each oligomer of length N differs from the corresponding (N−1)-mer by an additional nucleotide at the 3' terminus of the chain. We thus considered that the 3' terminal dideoxynucleotides of each oligomer may be specific determinants of the variance of relative separation. FIG. 3A shows relative separations of those oligonucleotide chains terminating with dideoxypyrimidines. A nearly total partition of these species is apparent. The chains with 3' ddT are consistently slower than average over the range of 400 nucleotides length. Those terminating with 3' ddC are consistently faster than average. The relative temporal separations of dideoxypurine-terminated oligomers, FIG. 3B, are closer to the average than are those with 3' dideoxypyrimidines. Statistically, chains ending with 3' ddG are slower than average and those with 3' ddA are faster than average. The average relative separations of these groups of oligomers, based on the 3' dideoxynucleotide, are presented in Table 1. There is a statistically significant gradient of relative separations, increasing in the following order:

(faster) - - - ddC <- - - ddA <- - - ddG <- - - ddT (slower).

This relation between the identity of the 3' dideoxynucleotide and mobility of the oligomer applies to DNA samples in which the reporting fluorophore is attached to the individual 3' dideoxynucleotide terminators or to the 5' end of the DNA sequencing primer. The difference between the average relative separations of the most similar groups, those with 3' dideoxypurines, corresponds to 3 to 4 standard errors of mean (probability $p < 0.001$ that the differences are due to random variation alone). The most distinct oligomer groups, those with 3' dideoxypyrimidines, have means which differ by 14 to 17 times the standard error. The probability that this is due to chance alone is infinitesimal, $p < 10^{-40}$).

Two different groupings of the data were evaluated as negative controls. The variation of relative separation was analyzed for four groups with respect to the identity of nucleotide (N+1), the next nucleotide of the DNA sequence, which is not physically part of the labeled oligomer of length (N). The oligomers were also analyzed as four groups according to length and without regard to their 3' terminal nucleotides. None of these control groups differs significantly from the total group of oligomers in terms of average relative separations, $1.00 \pm 0.19$. The variance associated with average relative separation in each of these negative control groups was consistently greater than for any of the groups based on the identity of the 3' dideoxynucleotide.

We next evaluated the possible role of the 3' proximal deoxynucleotide (N−1) as a co-determinant of the variance of relative temporal separation of oligomers. An array of distributions, based on the sixteen possible 3' terminal dinucleotide sequences, FIG. 4, leads to the generalization that relative temporal separations increase in the order (faster) - - - dT-ddN < - - - dR-ddN < - - - dC-ddN (slower).

Figure 4:
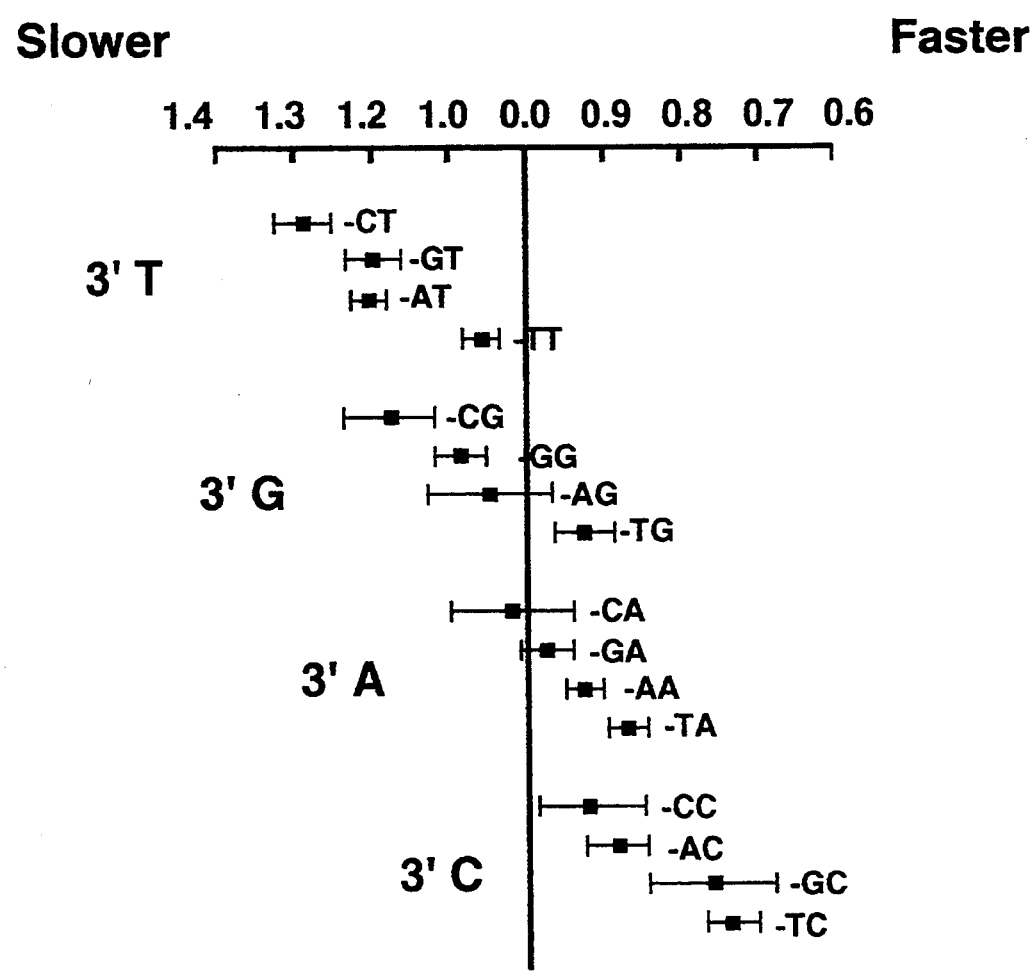
FIG. 4 shows that the relative separations of oligonucleotides are correlated with the 3' terminal dinucleotide sequences.

In FIG. 4, the relative separations of the M13 mp18 oligomers were sorted according to the 16 possible 3' terminal dinucleotide combinations. The groups are arranged from slower to faster, in the order 3'-ddT, -ddG, -ddA, -ddC. The black squares indicate the average relative separation for each group; the error bars correspond to the standard deviation of values for each group. The groups of faster and slower oligomers are symmetrically distributed about the average relative temporal separation. Statistically indistinguishable results were obtained from ladders which were generated with unlabeled dideoxynucleotides and a fluorescent dG-505 labeled 5' primer.

It is interesting to note that the pyrimidines are associated again with the most extreme differences in mobility, but they contribute in opposite order when located in the 3' proximal and 3' terminal positions. The same order and magnitudes of results were obtained with the reporter fluorophores placed at the 3' end or the 5' end of the oligomers (results not shown).

Figure 5A:
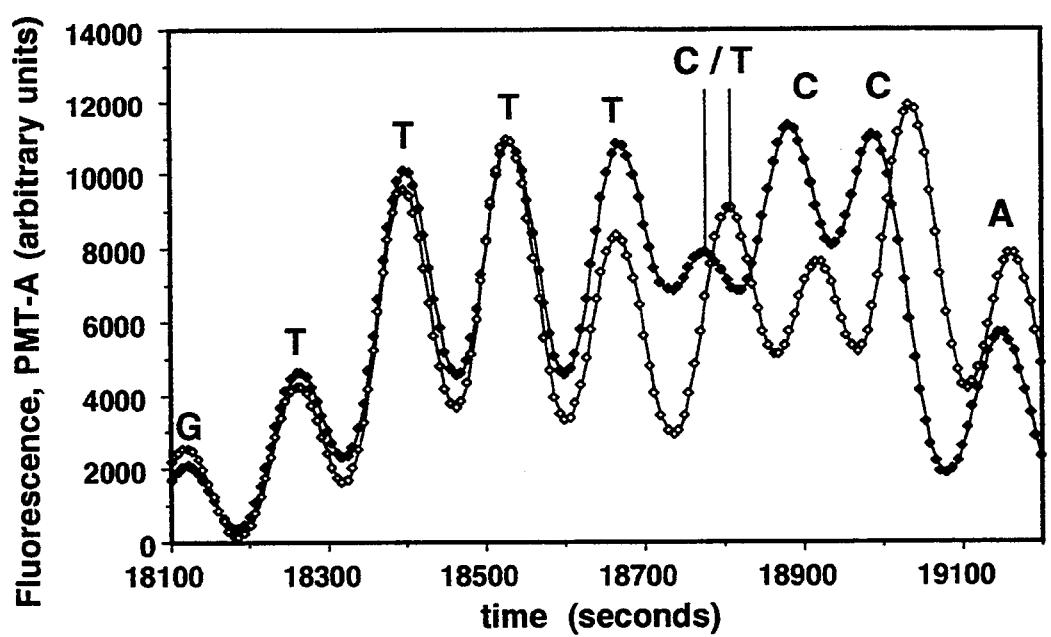
FIG. 5 shows data streams obtained from DNA sequences which differ by a single base change.
Figure 5B:
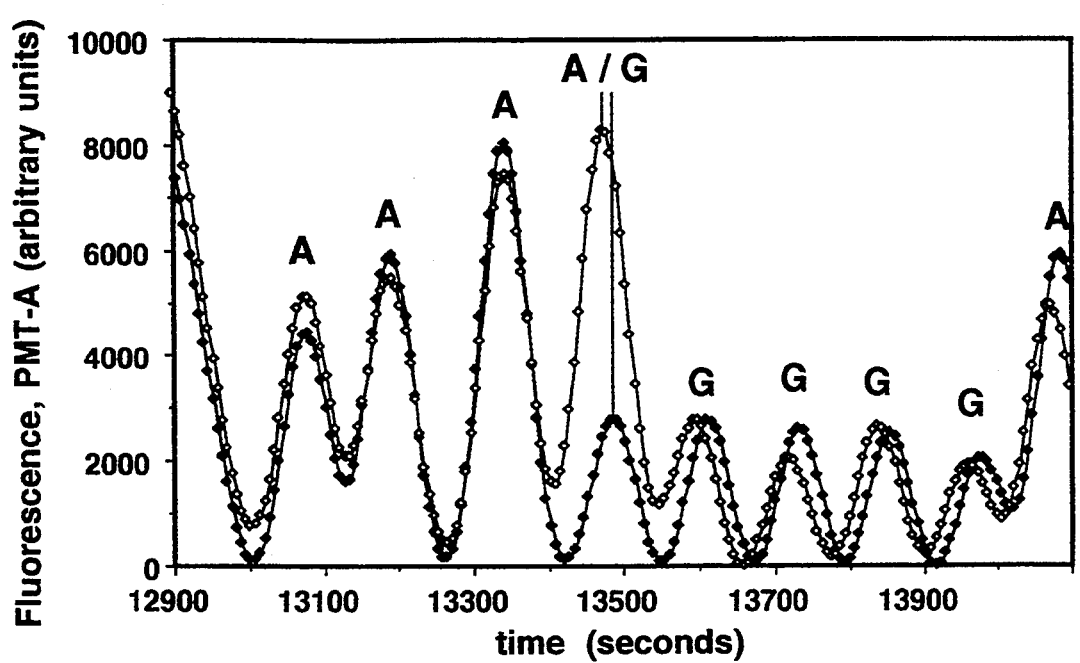
Figure 5C:
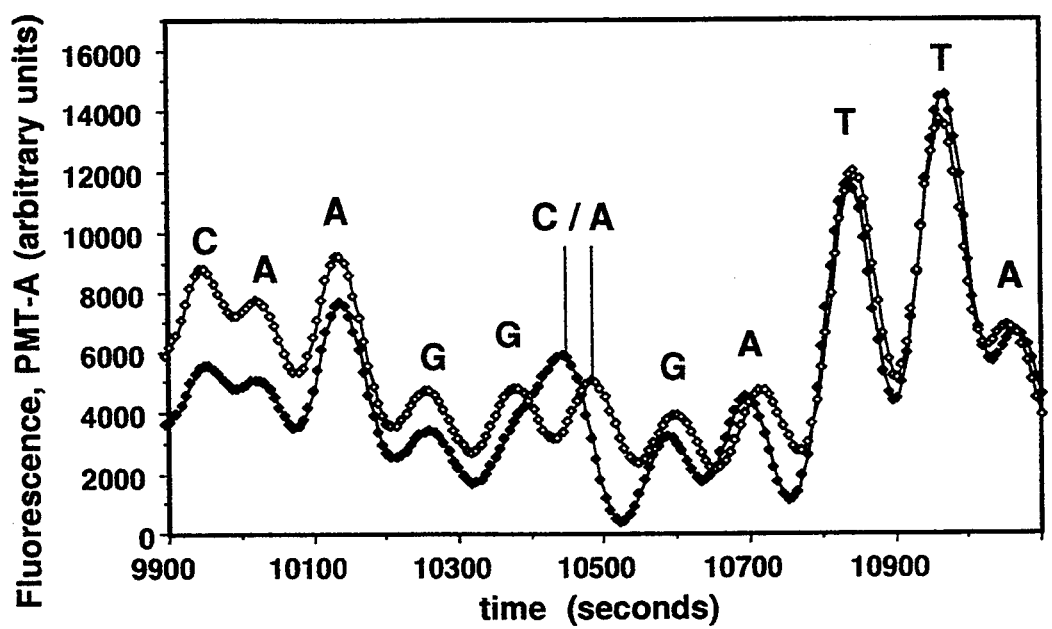

FIG. 5 shows parallel data streams from the DNA sequencing ladders of wild type M13 mp18 and three mutants which differ by single base changes. Data from only one of the two photometers is shown for each sample. For each comparison, the wild type and mutant DNA data streams (PMT-A channel only) were aligned by superposition of the ladders through the oligomers preceding the base difference. This is accomplished with a single shift of one data stream by no more than one or two scan intervals. Such alignment is maintained over thousands of scans of identical sequences.

The base changes distinguish the parallel ladders of wild type and mutant oligonucleotides which, up to the points of the lesions, are physically identical and indistinguishable in terms of their relative temporal separations of successive oligomers. Beyond the locus of base differences, the longer oligomers inherit altered mobilities; the data streams become asynchronous at the positions corresponding to the base changes of the mutants. Thus oligomers which are identical through their first (N−1) deoxynucleotides, have different mobilities due to their different 3' dideoxynucleotide terminators at position (N). The data streams of these and other mutants we have screened are consistent with the conclusions derived above by reference to average separations of oligomers.

A second feature of the parallel data streams for wild type and mutant DNA is that they continue asynchronously beyond the position of base change. This suggests that conformational differences due to the interactions involving the 3' terminal and proximal nucleotides are inherited by longer oligomers, at least in part, as local structure at that position.

Thus, local, nucleotide-specific interactions lead to differences in the mobilities of homologous oligonucleotides in DNA sequencing ladders. A systematic variation of conformation and mobility is apparent, determined by the sequence of two to three adjacent, 3' terminal nucleotides. Oligomers with 3'-ddT migrate more slowly than expected on the basis of length alone, and thus are better separated from the preceding, shorter oligomers in the sequencing ladder. Oligomers with 3'-ddC are relatively faster than expected, and are therefore less separated. At the 3' penultimate position, -dC- increases and -dT-reduces separation. Purines at the 3' terminal or penultimate positions of oligonucleotides affect separation less than the pyrimidines. These results lead us to conclude that the nucleotides on the single strand are able to interact with one another and thus induce conformational changes that affect the oligomer's mobility.

The above rules regarding the effect of terminal DNA sequence on the mobility of an oligomer can be incorporated in base-calling processes to improve the accuracy of the identification of the nucleic acid sequence. For instance, neural networks trained with an intensity variable, such as fluorescence ratio, only do not perform as well as networks trained with input of both separation and ratio data for each oligomer. With both input parameters, accuracy improves consistently from 92–94% to 98% correctly specified bases in sequence.

Figure 6A:
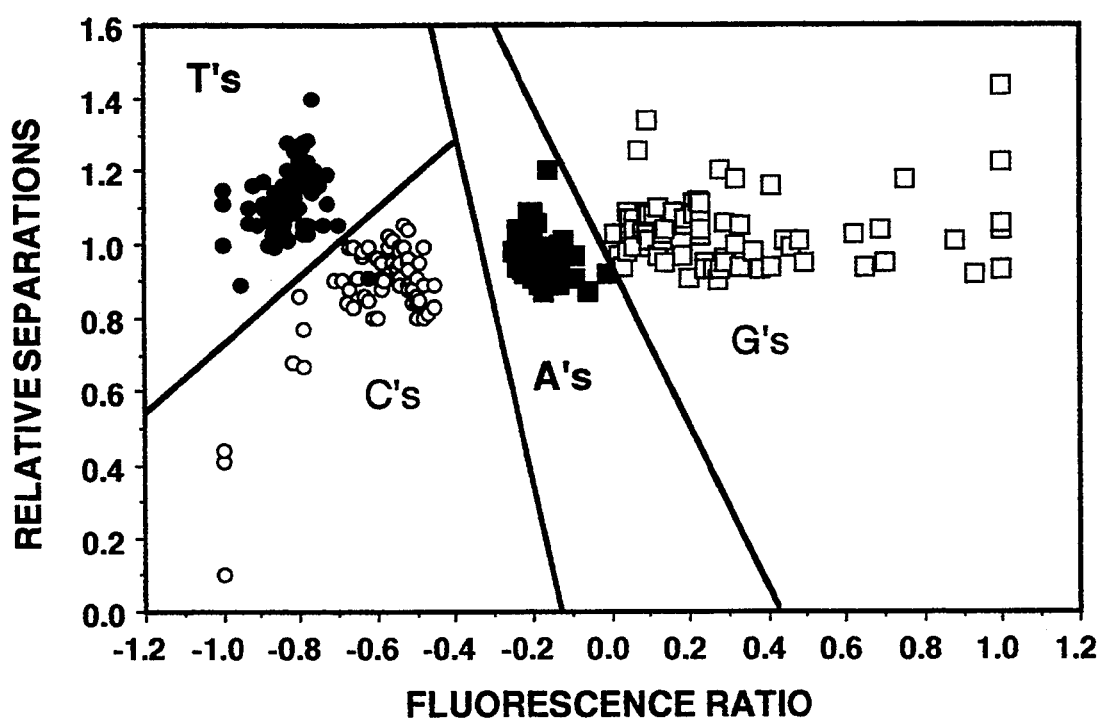
FIG. 6 provides scatter plots for two different DNA samples of 271 and 340 nucleotides that show the partitioning of terminal nucleotides with fluorescence ratios and relative separations.
Figure 6B:
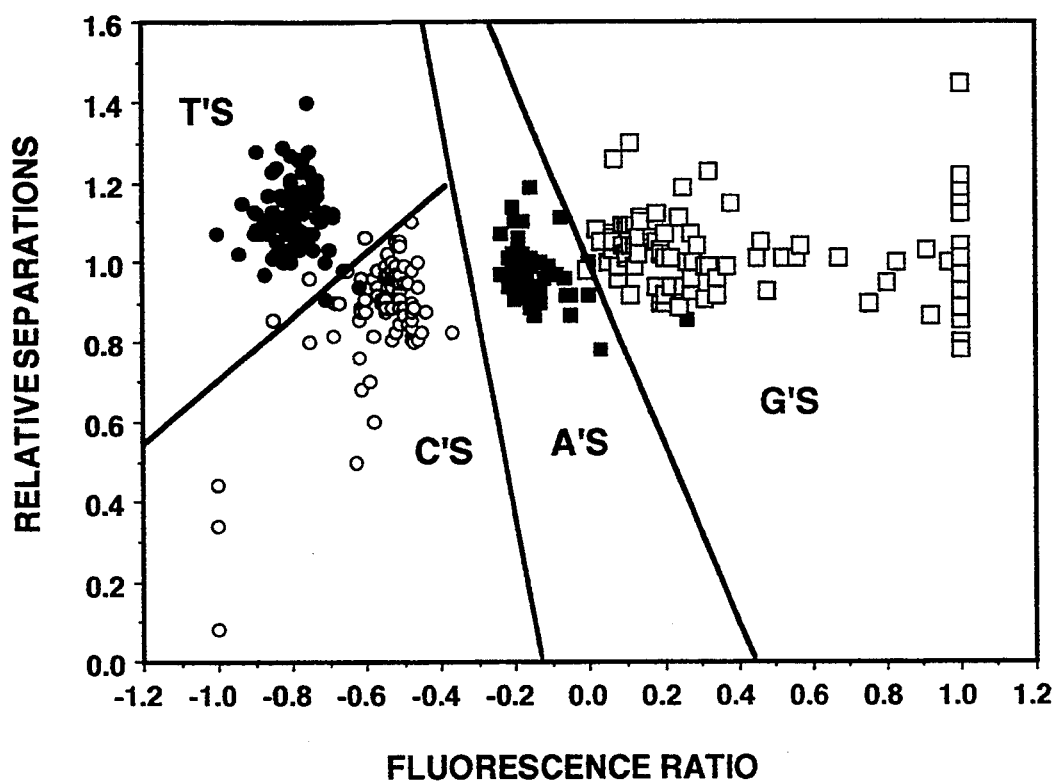

Furthermore, expert system methods can be used. For instance, as shown in FIG. 6, a scatter plot of fluorescence ratios and relative separations for DNA samples contributes to more accurate partitioning of the DNA sequencing data into the four classes of terminal dideoxynucleotide identity. FIG. 6 shows two scatter plots of fluorescence ratios and relative separations for two different DNA samples of 271 and 340 nucleotides. The individual points are coded according to the known identities of the 3' dideoxynucleotides. Four separate domains are clearly evident, although the partition is not fully discrete in the data space. In each sample, a few purines and several pyrimidines overlap in a way that impedes distinctions as A or G and T or C.

Using ratio alone as a discriminator (three vertical lines at boundary values of ratios, not shown), the minimum number of miscalls represent a maximum accuracy of 94–95%. If three diagonal lines are used to segregate the four domains of data, based on both ratio and separations, then the minimum number of miscalls represents a maximum accuracy of 98–99%. The same diagonal discriminator lines are used in the plots for each of the two DNA sequences.

A rule-based expert system could use the functions associated with the three line (or more complex curves) to establish base identity as a function of the two variables, ratio and separation. A neural network trained for such data sets effectively optimizes the partition of classes by evolution of connection weights to evaluate functionality equivalent to the discriminator lines (or planes). With similar data sets, generated with comparable nucleotide reagents, each approach has consistently increased the accuracy of basecalling from 92–95% to about 98% correct assignments.

Use of Relative Oligomer Yields as an Informative Variable in Nucleic Acid Sequencing If each base has an equal affinity to being incorporated onto the complementary strand by the polymerase during replication, uniform intensity profiles would result in the oligomer ladders. However, it has long been recognized that variations in band intensities do occur; these variations appear regardless of the type of label used, radioactive or fluorometric and, in this DNA sequencing ladder context, are correlated to the number density of molecules in the signal.

Variations in signal intensities have been investigated using different polymerases in an effort to produce more uniform peak heights. Experiments have also been conducted in which either Mg or Mn was added during the replication process to yield more uniform profiles or amplify the differences, respectively. However, our analysis indicates that within these intensity variations is information indicative of local DNA sequence. Thus, patterns and rules can be identified and used to supplement basecalling procedures to further refine the accuracy of the finished DNA sequence.

As shown in FIG. 5, not only does the local nucleic acid sequence affect the relative separations of successive oligomers in the nucleic acid sequencing ladders, a particular nucleotide also affects the yields of oligomers at neighboring positions. FIG. 5 overlays the signal profiles from the same detection photometer for two nucleic acid samples having identical sequences except at one position. Peak times and heights are essentially identical up to the position of the changed nucleotide but, even though the downstream sequences are identical, the intensity profiles are different. It appears that the local sequence is affecting the efficiency of the polymerase to incorporate nucleotides during replication. Thus, relative oligomer yields are determined by competition between pools of deoxynucleotides and dideoxyterminators in a manner that is dependent upon DNA sequence in the immediate locale of DNA chain elongation. This type of behavior would produce variations in the number density of oligomers and the corresponding changes in the relative intensities of successive peaks.

Thus, the relative intensities of successive signals, which corresponds to the relative yields of labeled oligomers in ladders, comprise an informative variable related to the local nucleic acid sequence. Similar to the treatment above with respect to the informative variable relating to the relative separations between successive signals, either expert systems or neural networks trained with data that includes this new variable can be employed to further improve basecalling accuracy.

Figure 7:
FIG. 7 shows the proposed hairpin loop and extended conformations of a DNA sequence subject to compression artifacts.
Figure 7:
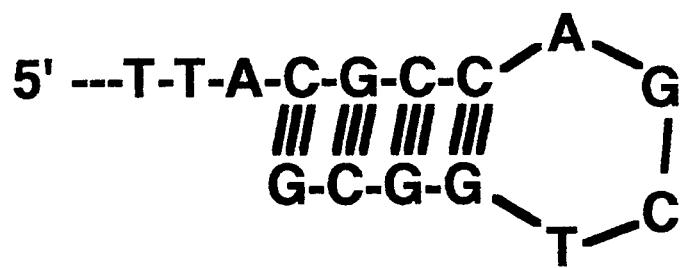

A compression artifact is an extreme departure from the typically normally ordered peak to peak separations based upon mobility and length. A single base difference in a DNA sequence can determine whether an oligonucleotide sequencing ladder appears with a compression artifact. For instance, the proposed hairpin loop and extended conformations of the DNA shown in FIG. 7 and SEQ ID No:1 are subject to a compression artifact. The asterisk indicates the dC residue of the sequence which is changed in a mutation whose DNA no longer exhibits the downstream compression artifact. Oligomers of the compression-prone sequence and those of the mutant comigrate up to the dG residue which is underlined in the lower structure. The compression involves the next two oligomers, indicating at least three base pairs are required to stabilize, if only transiently, such a small hairpin structure. The detailed analysis, particularly in a neural network, of the intensities and relative separations can characterize such artifacts and permit interpretation of the sequence prior to such artifacts.

Pattern Recognition of Base Sequences

A variety of pattern-recognition based procedures have focused on problems related to information embedded as short domains within long DNA sequences. Many applications have rewarded efforts with successful identification of signals associated with known biological functions. Such programs have searched vast arrays of nucleic acid sequence in data banks to identify candidate transcriptional promoters and terminators, RNA splicing sites and ribosome binding sites.

Similarly, a pattern-recognition approach can be used to correlate either raw data stream sequence information or data stream information that has been processed by the enhanced resolution process of the instant invention as described above with finished nucleic acid sequences. This correlation can be used either directly to produced finished nucleic acid sequences or in combination with any of the above-listed informative variables to produce a more accurate finished sequence in a rule-based expert system. Pattern arrays encompassing 2 or more bases, preferably 3 to 11 bases, most preferably 3–7 bases, can be compared with template patterns to provide the requisite information. A pattern recognition factor, which expresses the correlation between the pattern arrays derived from the data stream and previously compiled template patterns, can be used to express this information in an expert system. For instance, a pattern recognition factor derived from the comparison of the relative separations and intensities of adjacent signals from the data stream with templates can be used to express the degree of this correlation.

For instance, considering pattern arrays of five bases in a row, there are $4^5$ or 1,024 different arrays of combining the four bases (A, G, C, and T) five in row. Thus, acquisition of 5,000–10,000 bases of raw data sequence is necessary to obtain representative examples of each of these combinations. Because raw data streams processed by the second derivative, signal extraction process of the instant invention are more suitable as templates for pattern recognition, it is preferable to convert data streams from both the template patterns and test arrays using this process.

Expert-system rule based interpretation of sequence can exploit the relative separation variable and its relationship with the terminal nucleotides of an oligomer. Also, the use of the relative separation variable in conjunction with factors known to affect the intensity of certain oligonucleotide signals can be useful in building an expert system. For instance, it is common experience that in sequencing ladders generated by the Klenow polymerase, the second C or second G is the most intense nucleotide in runs of C's and G's. Similarly, the first A or first T is the most intense in runs of A's or T's. With T7 polymerase, C nucleotides tend to be weak when they follow T's in the sequencing ladder. Furthermore, T7 polymerase incorporates SF526-ddTTP with difficulty and labeled T's following purines are particularly weak. In the presence of $MnCl_2$ and T7 polymerase, the variation of intensity for each nucleotide may be supressed and, under these conditions, the yields are primarily determined by the ratio of terminators to deoxynucleotides. While this latter procedure can facilitate visual inspection of sequencing ladders, it can also sacrifice information that can be exploited by an expert-based system to more accurately determine nucleic acid sequence.

Alternatively to this above pattern-recognition approach, neural networks provide a practical tool for translation of raw sequencer data to DNA sequences. Input data can comprise any of the informative variables discussed above, either alone or in combination. Thus, neural networks provide a mechanism to implement the procedures discussed above for determining an improved nucleic acid sequence using the above-discussed informative variables. Furthermore, similar to the template patterns discussed above, neural networks can be used as a pattern-recognition tool which utilizes information from two or more signals to determine nucleic acid sequence at a particular signal position. Thus, perturbations on information variables, such as relative separations and relative intensities between signals, which are caused by the influence of neighboring bases, can be correlated to allow accurate determination of the nucleic acid sequence. The neural network can include information derived from signals corresponding to two or more bases, preferably 3 to 11 bases, most preferably 3-7 bases.

Figure 8:
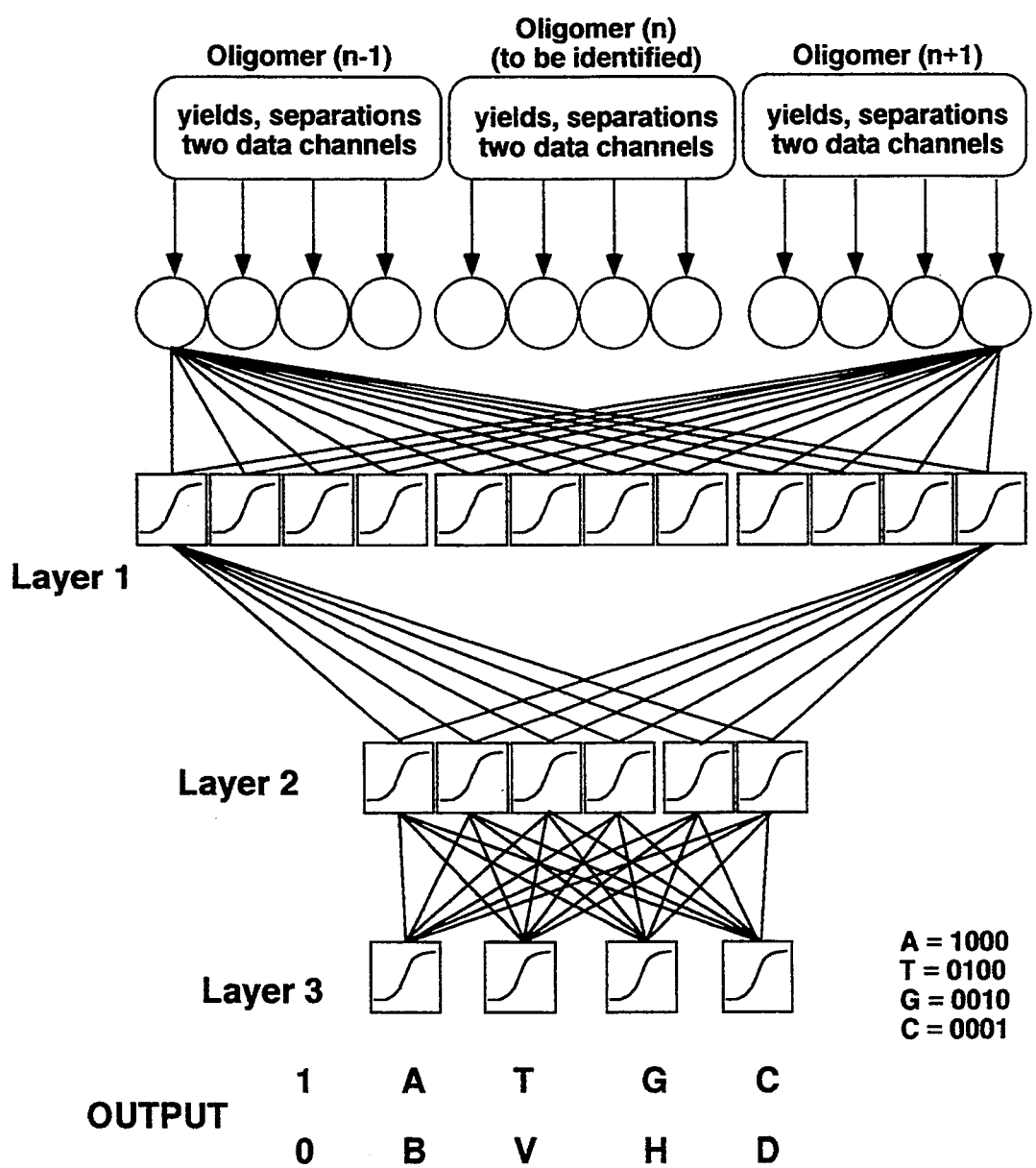
FIG. 8 models a three-level neural network.

A simple model of a three layer network, comprised of an input processor array, a hidden layer array of processors and a final output array of four units that is used to translate raw data streams to DNA sequences is illustrated in FIG. 8. Input data correspond to informational variables, such as the separation times and intensity measurements from the PMT-A and PMT-B data channels. Input array and processing arrays can be enlarged to accept data representing 5, 7, 9 or more oligomers. In FIG. 8, only outermost connections are shown in the upper layers.

Referring to FIG. 8, Layer 1 represents the input data values, which are multiplied by weights for each processor. In Layer 2, the sums of Layer 2 inputs give net-threshold values, which are converted to outputs with squashing functions. Outputs are multiplied by the hidden layer's weight array. In Layer 3, the sums of Layer 3 inputs are converted to outputs with squashing functions. These outputs are compared, with the largest unit of the array is set to 1 while the others are set to 0. As an ordered array, the result is interpreted as a 4 bit number, using the representation: 1000=>A; 0100=>T; 0010=>G; 0001=>C. These values are compared to that expected from the training set of sequences. Errors are back propagated to adjust the weights at each level before the next trial is run.

The goal of the network is to process the input data array and reliably predict the-terminal nucleotide of the middle oligomer. For simplicity, the input array only shows three oligomers, labeled n−1, n (to be identified) and n+1.

Table 2 show portions of a typical input and expected output fields of a training/testing file for a small network (NeuralWorks' neural network development shell, Explorer package Neura/Ware, Pittsburg, Pa. The input file provides six data fields associated with each oligomer to be identified: (a) the relative separation of oligomer n from n−1; (b) the ratio of yield of oligomer n to that of n−1 in the PMT-A channel; (c) the yield (arbitrary units of fluorescence) of oligomer n in PMT-A channel; (d) the ratio of yield of oligomer n to that of n−1 in the PMT-B channel; (e) the yield (arbitrary units of fluorescence) of oligomer n in PMT-B channel and (f)the natural logarithm of the oligomer's signal ratio, ln[PMT-B/PMT-A]. The maximum signal from the four output nodes is used to identify the base in question. The network has six input buffer nodes, four output nodes, and two hidden layers of six and four processing nodes. Table 2 presents 20 records representing 20 successive oligomers in a DNA sequencing ladder.

TABLE 2

| Repl. Sep'n | Input Data Fields (6) | | | | | Expected Output Fields (4) for Training | | | |
|---|---|---|---|---|---|---|---|---|---|
| | (n/n−1)$^a$ | PMT-a | (n/n−1)$^b$ | PMT-b | ln(b/a) | G? | A? | C? | T? |
| 1.2 | 1.46 | 21774 | 0.31 | 2989 | −1.99 | 0 | 0 | 0 | 1 |
| 1.02 | 0.42 | 9166 | 0.26 | 773 | −2.47 | 0 | 0 | 0 | 1 |
| 0.86 | 1.98 | 18159 | 7.78 | 6016 | −1.1 | 0 | 0 | 1 | 0 |
| 1.1 | 0.26 | 4670 | 0.94 | 5626 | 0.19 | 1 | 0 | 0 | 0 |
| 1.03 | 2.2 | 10269 | 0.16 | 899 | −2.44 | 0 | 0 | 0 | 1 |
| 0.92 | 1.27 | 13031 | 9.99 | 8978 | −0.37 | 0 | 1 | 0 | 0 |
| 0.95 | 1.16 | 15135 | 1.06 | 9512 | −0.46 | 0 | 1 | 0 | 0 |
| 1.14 | 0.74 | 11180 | 0.1 | 946 | −2.47 | 0 | 0 | 0 | 1 |
| 0.85 | 1.59 | 17781 | 6.09 | 5757 | −1.13 | 0 | 0 | 1 | 0 |
| 1.01 | 1.03 | 18321 | 2.1 | 12085 | −0.42 | 0 | 1 | 0 | 0 |
| 1.1 | 0.47 | 8525 | 0.07 | 809 | −2.35 | 0 | 0 | 0 | 1 |
| 0.99 | 0.66 | 5586 | 8.43 | 6819 | 0.2 | 1 | 0 | 0 | 0 |
| 1.03 | 0.76 | 4268 | 0.69 | 4730 | 0.1 | 1 | 0 | 0 | 0 |
| 1.06 | 1.32 | 5630 | 0.08 | 388 | −2.67 | 0 | 0 | 0 | 1 |
| 0.88 | 3.13 | 17599 | 14.17 | 5499 | −1.16 | 0 | 0 | 1 | 0 |
| 0.99 | 0.89 | 15704 | 1.94 | 10689 | −0.38 | 0 | 1 | 0 | 0 |
| 1.07 | 1.1 | 17347 | 0.14 | 1484 | −2.46 | 0 | 0 | 0 | 1 |
| 0.92 | 0.87 | 15067 | 7.06 | 10480 | −0.36 | 0 | 1 | 0 | 0 |
| 0.95 | 0.14 | 2059 | 0.36 | 3738 | 0.6 | 1 | 0 | 0 | 0 |
| 0.91 | 8.24 | 16976 | 1.35 | 5047 | −1.21 | 0 | 0 | 1 | 0 |

Networks, such as the ones discussed above, can be trained using half the data of one DNA sequence file for training and the other half for evaluation. Alternatively, entire files have been used for training (including files of up to 400 bases of sequence). The network is then tested on similar data files representing the same or different DNA sequences from parallel tracks of the same gel and/or from different gels.

Figure 9:
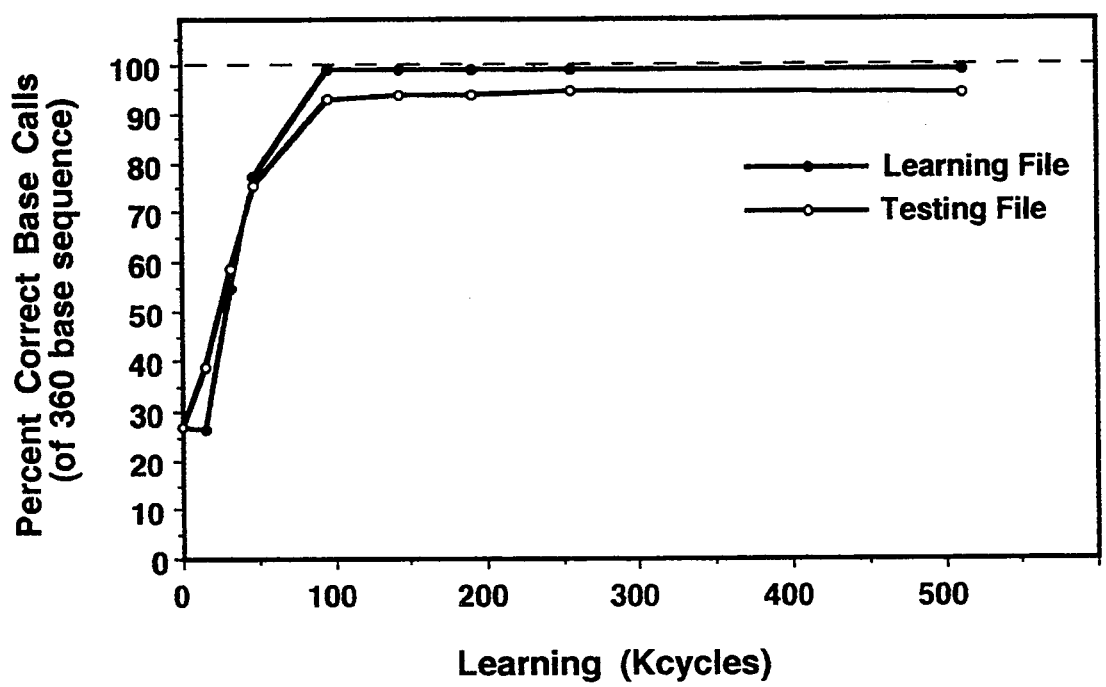
FIG. 9 shows learning curves for DNA sequences of 306 nucleotides after different extents of random cycle training of a neural network.

FIG. 9 illustrates typical learning curves for evaluation on the training and testing files after different periods of random cycle training of the network described in conjunction with Table 2. FIG. 9 shows learning curves for DNA sequences of 306 nucleotides, from both the file used for training and a parallel file never seen by the network during training. Performance of the network is evaluated as the percent of correct base calls. These results, when analyzed in detail, follow closely the documented experience with such neural networks in the area of text to speech translation or morphometric taxonomical classifications.

Table 3 shows a segment of a typical expected (SEQ. ID NO: 2) and actual output file. This table presents a portion of an output file generated during testing of the trained network described in conjunction with Table 2. Results for 20 successive nucleotides are illustrated, one of which is incorrectly identified as a 3'T instead of a 3'A.

TABLE 3

|    | Expected Results | | | | Actual Results | | | |    |
|----|----|----|----|----|-------|------|-------|------|----|
| 5' | G? | A? | C? | T? | G?    | A?   | C?    | T?   | 5' |
| T  | 0  | 0  | 0  | 1  | −0.01 | 0.10 | −0.02 | 1.00 | T  |
| A  | 0  | 1  | 0  | 0  | 0.00  | 0.20 | −0.32 | 0.08 | A  |
| A  | 0  | 1  | 0  | 0  | 0.00  | 0.20 | −0.30 | 0.07 | A  |
| T  | 0  | 0  | 0  | 1  | 0.00  | 0.07 | −0.20 | 1.18 | T  |
| C  | 0  | 0  | 1  | 0  | −0.01 | 0.22 | 1.01  | 0.01 | C  |
| A  | 0  | 1  | 0  | 0  | 0.01  | 0.18 | −0.33 | 0.21 | T or A |
| T  | 0  | 0  | 0  | 1  | 0.00  | 0.08 | −0.16 | 1.14 | T  |
| G  | 1  | 0  | 0  | 0  | 0.98  | 0.04 | −0.33 | 0.02 | G  |
| G  | 1  | 0  | 0  | 0  | 0.98  | 0.04 | −0.33 | 0.02 | G  |
| T  | 0  | 0  | 0  | 1  | 0.00  | 0.07 | −0.18 | 1.16 | T  |
| C  | 0  | 0  | 1  | 0  | −0.01 | 0.20 | 0.86  | 0.13 | C  |
| A  | 0  | 1  | 0  | 0  | 0.02  | 0.19 | −0.33 | 0.13 | A  |
| T  | 0  | 0  | 0  | 1  | −0.01 | 0.10 | −0.02 | 1.00 | T  |
| A  | 0  | 1  | 0  | 0  | 0.01  | 0.20 | −0.33 | 0.09 | A  |
| G  | 1  | 0  | 0  | 0  | 0.98  | 0.04 | −0.33 | 0.01 | G  |
| C  | 0  | 0  | 1  | 0  | −0.01 | 0.22 | 1.00  | 0.01 | C  |
| T  | 0  | 0  | 0  | 1  | −0.01 | 0.09 | −0.10 | 1.08 | T  |
| G  | 1  | 0  | 0  | 0  | 0.98  | 0.04 | −0.33 | 0.02 | G  |
| T  | 0  | 0  | 0  | 1  | 0.00  | 0.08 | −0.15 | 1.13 | T  |
| T  | 0  | 0  | 0  | 1  | −0.01 | 0.10 | −0.03 | 1.00 | T  |
| 3' |    |    |    |    |       |      |       |      | 3' |

Table 4 describes the results of basecalling with a trained network on the data from the training file and a parallel test file, from shorter to longer oligomers of the sequencing ladder. A high level of performance is demonstrated from the early region (shorter oligomers) through the data into the region of the longer oligomers. These results show that the trained network is capable of evaluating similar data beyond the data used for training.

TABLE 4

|            | Percent Correct Calls | |
|------------|-----------|-----------|
| Length (n) | Learn File | Test File |
| 61–120 | 98.3 | 100.0 |
| 61–180 | 99.2 | 99.2  |
| 61–240 | 97.2 | 97.2  |
| 61–300 | 98.3 | 98.3  |
| 60–350 | 97.7 | 97.1  |

Table 5 presents the analysis of performance of a trained network in comparison with the two most recent versions of commercial basecalling software used to evaluate the same raw data files, BC4.0b16 and BC 5.0b1 (Basecaller Du Pont Genesis Software, Wilmington, Del.). The same raw data files were processed through the standard procedures of the commercial programs or pre-processed using the n=4 and m=6 smoothed second derivative process used to generate input for the trained neural network. Evaluation was performed on both the training and testing files of two DNA sequencing samples. Neither the 4.0b16 or 5.0b1 versions were able to read these files beyond 300 bases and the version 5.0b1 program was only able to translate and specify sequence from one of these two files. In this example, the performance of the network was superior throughout the data range.

TABLE 5

|            | Percent Correct Calls | | |
|------------|---------|---------|---------|
| Length (n) | Network | BC 4.0b16 | BC 5.0b1* |
| 61–120 | 99.2 | 97.5 | 98.3 |
| 61–180 | 99.2 | 94.6 | 99.2 |
| 61–240 | 97.2 | 93.9 | 95.6 |
| 61–300 | 98.3 | 94.0 | 93.8 |
| 60–350 | 97.4 | —    | —    |

These results strongly support the feasibility of exploiting neural network programming to support the translation of raw sequencer data to finished DNA sequences. Even with the use of very small training sets (ca. 500 bases) and small networks, the networks have demonstrated performance superior to the large-scale deterministic programs which are the basis of the commercial base-callers. Furthermore, these results confirm the sequence-specific information available in the raw data streams at the level of relative yields and separations of the successive oligomers. These parameters are not used to advantage in any of the prior art, deterministic base-calling programs. Enhanced network performance, approaching 100% accuracy in basecalling, can be obtained from the use of large-scale networking programs and routine optimization of the program.

Modifications and variations of the present invention will be obvious to those skilled in the art from the foregoing detailed description of the invention. Such modifications and variations are intended to come within the scope of the appended claims.

What is claimed is:

1. A method for the nucleic acid sequence determination of a polynucleotide, wherein a nucleic acid sequencing ladder comprises signals corresponding to oligonucleotides formed from the polynucleotide, comprising the step of correlating an intensity variable for each signal in the nucleic acid sequencing ladder with an informative variable for that signal, wherein the informative variable comprises information from at least two adjacent signals from other than a tri-nucleotide palindrome in the nucleic acid sequencing ladder, such that each signal in the nucleic acid sequencing ladder is identified so as to determine the nucleic acid sequence corresponding to the polynucleotide.

2. The method of claim 1, wherein the informative variable comprises the relative separation between the signal and a signal adjacent to the signal in the sequencing ladder.

3. The method of claim 1, wherein the informative variable comprises the relative intensity between a signal and a signal adjacent to the signal in the sequencing ladder.

4. The method of claim 1, wherein the informative variable comprises a pattern recognition factor formulated by comparing, with a multiplicity of pattern recognition templates, the combination of the relative separation and the intensity for the signal and the relative separation and the intensity for at least one signal adjacent to the signal.

5. The method of claim 1, wherein the signals comprise spectrochemically detected signals.

6. The method of claim 1, wherein the signals comprise radioactively detected signals.

7. The method of claim 1, wherein the polynucleotide is DNA.

8. The method of claim 1, wherein the correlation step comprises formulating a scatter plot.

9. The method of claim 1, wherein the correlation step comprises inputting the intensity variable and the informative variable into a trained neural network.

10. A method for the automated nucleic acid sequence determination of a polynucleotide, comprising the steps of:

a) obtaining at least one digitized data stream from at least one data channel of a nucleic acid sequencer, wherein the data stream comprises successive signals corresponding to oligonucleotides from other than a tri-nucleotide palindrome in a nucleic acid sequencing ladder formed from the polynucleotide;

b) locating the position of the maximum for each signal in the data stream;

c) measuring the intensity for each signal in the data stream to allow formulation of an intensity variable for each signal;

d) calculating an informative variable for each signal in the data stream, wherein the informative variable comprises position of maxima or intensities for at least two adjacent signals in the nucleic acid sequencing ladder; and c) correlating the informative variable for each signal with the intensity variable for each signal to determine the nucleic acid sequence corresponding to the polynucleotide.

11. The method of claim 10, wherein the informative variable comprises the relative separation between the signal and a signal adjacent to the signal in the sequencing ladder.

12. The method of claim 10, wherein the informative variable comprises the relative intensity between the signal and a signal adjacent to the signal in the sequencing ladder.

13. The method of claim 10, wherein the informative variable comprises a pattern recognition factor formulated by comparing, with a multiplicity of pattern recognition templates, the combination of the relative separation and the intensity for the signal and the relative separation and the intensity for at least one signal adjacent to the signal.

14. The method of claim 10, wherein the signals comprise spectrochemically detected signals.

15. The method of claim 10, wherein the signals comprise radioactively detected signals.

16. The method of claim 10, wherein the polynucleotide is DNA.

17. The method of claim 10, wherein the correlation step comprises formulating a scatter plot.

18. The method of claim 10, wherein the correlation step comprises inputting the intensity variable and the informative variable into a trained neural network.

19. The method of claim 10, wherein the locating step comprises:
   a) obtaining a smoothed second derivative for each point in the digitized data stream to produce a derivative digitized data stream, wherein each point of the derivative digitized data stream comprises the value of the smoothed second derivative for the corresponding point in the digitized data stream;
   b) replacing with zero, for each point in the derivative digitized data stream in which the value of the smoothed second derivative at the point is positive or zero, the value of the second derivative at the point in the derivative digitized data stream;
   c) multiplying by −1, for each point in the derivative digitized data stream in which the value of the smoothed second derivative at the point is negative, the value of the second derivative at the point in the derivative digitized data stream; and
   d) identifying all points in the derivative digitized data stream which possess a value greater than both the immediately preceding and successive points in the derivative digitized data stream.

20. The method of claim 10, wherein said obtaining step comprises acquiring a first digitized data stream from a first data channel and a second digitized data stream from a second data channel and the intensity variable for each signal comprises the ratio of the intensity of the signal in the first digitized data stream and the intensity of the signal in the second digitized data stream.

21. A method for the automated nucleic acid sequence determination of a polynucleotide, comprising the steps of acquiring an intensity variable and at least one informative variable for each signal contained in a nucleic acid sequencing ladder corresponding to the polynucleotide and correlating in a trained neural network the intensity variable and the at least one informative variable, wherein the informative variable comprises the relative intensity between a signal and a signal adjacent to the signal in the sequencing ladder.

22. A method for the automated nucleic acid sequence determination of a polynucleotide, comprising the steps of acquiring an intensity variable and at least one informative variable for each signal contained in a nucleic acid sequencing ladder corresponding to the polynucleotide and correlating in a trained neural network the intensity variable and the at least one informative variable, wherein the informative variable comprises the relative separation between a signal and a signal adjacent to the signal in the sequencing ladder.

23. A system for the automated nucleic acid sequence determination of a polynucleotide from a digitized data stream, wherein the digitized data stream comprises successive signals corresponding to oligonucleotides from other than a tri-nucleotide palindrome in a nucleic acid sequencing ladder formed from the polynucleotide, comprising:
   a) means for calculating an intensity variable for each signal in the digitized data stream;
   b) means for calculating an informative variable for each signal in the digitized data stream, wherein the informative variable comprises information from at least two adjacent signals in the nucleic acid sequencing ladder; and
   c) means for correlating the intensity for each signal with the informative variable for each signal to identify each signal in the nucleic acid sequencing ladder so as to determine the nucleic acid sequence corresponding to the polynucleotide.

24. The system of claim 23, wherein the means for calculating an informative variable comprise means for calculating the relative separation between the signal and a signal adjacent to the signal in the digitized data stream.

25. The system of claim 23, wherein the means for calculating an informative variable comprise means for calculating the relative intensity between a signal and a signal adjacent to the signal in the sequencing ladder.

26. The system of claim 23, wherein the means for calculating an informative variable comprise means for calculating a pattern recognition factor formulated by comparing the combination of the relative separation and the intensity for the signal and the relative separation and the intensity for at least one signal adjacent to the signal with a multiplicity of pattern recognition templates.

27. A system for the automated nucleic acid sequence determination of a polynucleotide, comprising:
   a) means for obtaining a digitized data stream from at least one data channel of a nucleic acid sequencer, wherein the data stream comprises successive signals corresponding to oligonucleotides from other than a tri-nucleotide palindrome in a nucleic acid sequencing ladder formed from the polynucleotide;
   b) means for calculating the position of the maximum for each signal;
   c) a memory associated with the calculating means;
   d) means for feeding to the memory the position of the maximum for each signal;
   e) means for storing in the memory an intensity variable for each signal in the data stream;
   f) means for calculating an informative variable for each signal in the digitized data stream, wherein the informative variable comprises information from at least two adjacent signals in the nucleic acid sequencing ladder;
   g) means for storing in the memory the informative variable for each signal;
   h) means for retrieving the intensity variable for each signal and the informative variable for each signal;
   i) means to correlate the intensity variable for each signal and the informative variable for each signal to identify each signal in the nucleic acid sequencing ladder so as to determine the nucleic acid sequence corresponding to the polynucleotide.

28. The system of claim 27, wherein the informative variable comprises the relative separation between the signal and a signal adjacent to the signal in the digitized data stream.

29. The system of claim 27, wherein the informative variable comprises the relative intensity between a signal and a signal adjacent to the signal in the sequencing ladder.

30. The system of claim 27, wherein the informative variable comprises a pattern recognition factor formulated by comparing the combination of the relative separation and the intensity for the signal and the relative separation and the intensity for at least one signal adjacent to the signal with a multiplicity of pattern recognition templates.

31. The system of claim 27, wherein the means for calculating the position of the maximum for each signal in the data stream comprises:
- a) means for calculating a smoothed second derivative for each point in the digitized data stream;
- b) means for storing in the memory a derivative digitized data stream, wherein each point of the derivative digitized data stream comprises the value of the smoothed second derivative of the corresponding point in the digitized data stream;
- c) means for replacing the value of the smoothed second derivative with zero for each point in the derivative digitized data stream in which the value of the smoothed second derivative at the point is positive with zero;
- d) means for multiplying the value of the smoothed second derivative by $-1$ for each point in the derivative digitized data stream in which the value of the smoothed second derivative at the point is negative; and
- e) means for identifying all points in the derivative digitized data stream which possess a value greater than both the immediately preceding and successive points.

32. The process of claim 31, further comprising, prior to step (a), the step of obtaining a smoothed first derivative for each point in the first digitized data stream and replacing each value of each point in the first digitized data stream with the value of the smoothed first derivative for the corresponding point of the first digitized data stream.

33. The process of claim 32, wherein the first derivative is smoothed over n data points, wherein $n=2$ to 25.

34. The process of claim 31, wherein the second derivative is smoothed over m data points, wherein $m=2$ to 25.

35. The process of claim 31, wherein the signals comprise signals from a mass spectrometer.

36. The process of claim 31, wherein the signals comprise chromatographic signals.

37. The process of claim 31, wherein the signals comprise digital imaging signals.

38. The process of claim 31, wherein the signals comprise signals from a nucleic acid sequencer.

* * * * *

UNITED STATES PATENT AND TRADEMARK OFFICE
CERTIFICATE OF CORRECTION

PATENT NO.   : 5,365,455
DATED        : November 15, 1994
INVENTOR(S)  : Tibbetts, et al It is certified that error appears in the above-identified patent and that said Letters Patent is hereby corrected as shown below:

In column 1, after line 3, insert a new paragraph to read:
-- This invention was made with government support under CA34126 awarded by the National Cancer Institute. The government has certain rights in the invention. --

Signed and Sealed this

Twenty-eighth Day of April, 1998

Attest:

BRUCE LEHMAN

Attesting Officer

Commissioner of Patents and Trademarks